(12) United States Patent
Mou et al.

(10) Patent No.: US 12,235,016 B2
(45) Date of Patent: *Feb. 25, 2025

(54) PURIFICATION DEVICE FOR EXERCISE ENVIRONMENT

(71) Applicant: Microjet Technology Co., Ltd., Hsinchu (TW)

(72) Inventors: Hao-Jan Mou, Hsinchu (TW); Ching-Sung Lin, Hsinchu (TW); Chin-Chuan Wu, Hsinchu (TW); Chi-Feng Huang, Hsinchu (TW); Yung-Lung Han, Hsinchu (TW); Chun-Yi Kuo, Hsinchu (TW); Chin-Wen Hsieh, Hsinchu (TW)

(73) Assignee: Microjet Technology Co., Ltd., Hsinchu (TW)

( * ) Notice: Subject to any disclaimer, the term of this patent is extended or adjusted under 35 U.S.C. 154(b) by 812 days.

This patent is subject to a terminal disclaimer.

(21) Appl. No.: 17/370,452

(22) Filed: Jul. 8, 2021

(65) Prior Publication Data

US 2022/0057091 A1 Feb. 24, 2022

(30) Foreign Application Priority Data

Aug. 21, 2020 (TW) ................................ 109128692

(51) Int. Cl.
*F24F 8/10* (2021.01)
*A61L 9/14* (2006.01)
(Continued)

(52) U.S. Cl.
CPC ................ *F24F 8/10* (2021.01); *A61L 9/145* (2013.01); *A61L 9/205* (2013.01); *A61L 9/22* (2013.01);
(Continued)

(58) Field of Classification Search
None
See application file for complete search history.

(56) References Cited

U.S. PATENT DOCUMENTS

| 2011/0086118 A1* | 4/2011 | Kim | B01D 53/34 |
| | | | 424/769 |
| 2017/0275472 A1* | 9/2017 | Yeung | A01N 65/22 |

(Continued)

FOREIGN PATENT DOCUMENTS

| CN | 209069775 U | 7/2019 |
| CN | 110501454 A | 11/2019 |

(Continued)

OTHER PUBLICATIONS

Geol, H. KR20080085964A—translated document (Year: 2008).*

*Primary Examiner* — Jelitza M Perez
(74) *Attorney, Agent, or Firm* — Birch, Stewart, Kolasch & Birch, LLP

(57) ABSTRACT

A purification device for exercise environment is provided and includes a main body, a purification unit, a gas guider and a gas detection module. The purification unit, the gas guider and the gas detection module are disposed in the main body to guide the gas outside the main body through the purification unit for filtering and purifying the gas, and discharge a purified gas. The gas detection module detects particle concentration of suspended particles contained in the purified gas. The gas guider is controlled to operate and export the gas at an airflow rate within 3 minutes. The particle concentration of the suspended particles contained in the purified gas, which is filtered by the purification unit, is reduced to and less than 0.75 μg/m³. Consequently, the purified gas is filtered, and an exerciser in an exercise environment can breathe with safety.

15 Claims, 34 Drawing Sheets

(51) Int. Cl.
  *A61L 9/20*   (2006.01)
  *A61L 9/22*   (2006.01)
  *F24F 1/0022*   (2019.01)
  *F24F 110/64*   (2018.01)

(52) U.S. Cl.
  CPC ....... *F24F 1/0022* (2013.01); *A61L 2209/111* (2013.01); *A61L 2209/134* (2013.01); *A61L 2209/14* (2013.01); *A61L 2209/22* (2013.01); *F24F 2110/64* (2018.01)

(56) References Cited

U.S. PATENT DOCUMENTS

| | | | |
|---|---|---|---|
| 2019/0212242 A1 | 7/2019 | Mou et al. | |
| 2019/0240371 A1* | 8/2019 | Benedek | B01D 53/8675 |
| 2020/0141608 A1 | 5/2020 | Sinha et al. | |
| 2020/0156084 A1 | 5/2020 | Mou et al. | |
| 2021/0299321 A1* | 9/2021 | Huang | A61L 9/205 |

FOREIGN PATENT DOCUMENTS

| | | | | |
|---|---|---|---|---|
| KR | 20080085964 A | * | 9/2008 | ............ A61L 9/205 |
| TW | 201738000 A | | 10/2017 | |
| TW | 201923290 A | | 6/2019 | |
| TW | I696816 B | | 6/2020 | |

\* cited by examiner

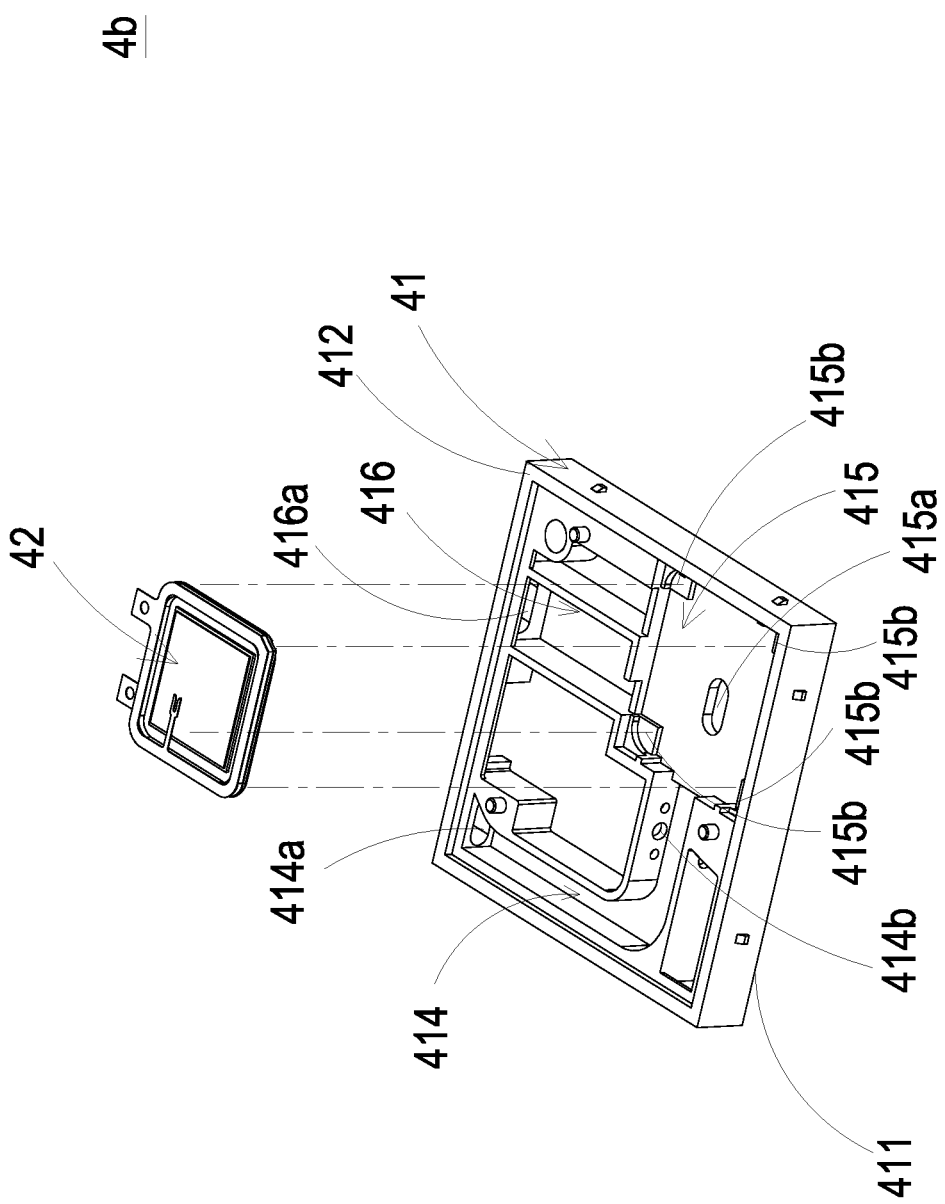

PURIFICATION DEVICE FOR EXERCISE ENVIRONMENT

FIELD OF THE INVENTION

The present disclosure relates to a purification device, and more particularly to a purification device for exercise environment combined with an exercise equipment which is applied in an exercise environment.

BACKGROUND OF THE INVENTION

The ventilation volume of human is about 10,000 liters per day without exercise, and it would become 10-20 times the normal amount when we exercise vigorously, especially during aerobic exercising. Exercising outdoors in the poor air condition, the dirt sucked into our body is beyond imagination and will cause a lot of burden on the cardiovascular system. Even young people with normal cardiovascular systems might suddenly appear some problems at this time. This would be harmful to their health or even their life accordingly.

As mentioned above, recently, people pay more and more attention to the quality of the air around their daily lives. For example, carbon monoxide, carbon dioxide, volatile organic compounds (VOC), PM2.5, nitric oxide, sulfur monoxide and even the suspended particles contained in the air that expose in the environment might be endanger to the human health, and even harmful for the human's life severely. For example, in a recent news report, an exerciser with a normal and healthy body running under a harsh environment and climate caused his sudden death and endangered his life as he breathed high concentration of PM2.5 during vigorous exercise. Therefore, the quality of environmental air has attracted the attention in various countries. Right now, people pay more attention to the air quality in the exercise environment. Therefore, the solution of how to provide purified air to avoid breathing harmful air and to monitor the air quality in real-time in the exercise environment is an issue of concern in the present disclosure.

SUMMARY OF THE INVENTION

An object of the present disclosure is to provide a purification device for exercise environment. A gas detection module is utilized to monitor the air quality in the exercise environment with the exerciser at any time, and a purification unit is utilized to provide a solution for purifying and improving the air quality. In this way, the gas detection module and the purification unit combined with a gas guider can export a gas at a specific airflow amount, so as to allow the purification unit to filter and obtain a purified gas. In addition, the gas guider constantly controls the airflow rate within 3 minutes to reduce the particle concentration of the suspended particles contained in the purified gas to less than 0.75 $\mu g/m^3$, so as to provide the purification by safe filtration. Moreover, the gas detection module is used to detect the breathing region around the nose of the exerciser in the exercise environment, so as to provide purified gas which has been safely filtrated for the exerciser to breath as doing exercise and obtain real-time information of the gas, so as to caution the exerciser in the exercise environment to take preventive measures, such as stop exercising, immediately, or using an isolation cover to keep exercising therein.

In accordance with an aspect of the present disclosure, a purification device for exercise environment which is applied in the exercise environment is provided and includes a main body, a purification unit, a gas guider and a gas detection module. The main body includes at least one gas inlet and at least one gas outlet. The purification unit is disposed in the main body for purifying a gas introduced into the main body through the at least one gas inlet. The gas guider disposed in the main body is adjacent to the at least one gas outlet, wherein the gas outside the main body is inhaled and flows through the purification unit for filtering and purification, so that a purified gas is filtered and discharged out through the at least one outlet. The gas detection module is disposed in the main body for detecting a particle concentration of suspended particle contained in the purified gas filtered through the purification unit. The gas guider is constantly controlled to operate and export a gas at an airflow rate within 3 minutes to filter and reduce the particle concentration of the suspended particles contained in the purified gas to less than 0.75 $\mu g/m^3$, so as to provide the purified gas through safe filtration to an exerciser for breathing in the exercise environment.

BRIEF DESCRIPTION OF THE DRAWINGS

The above contents of the present disclosure will become more readily apparent to those ordinarily skilled in the art after reviewing the following detailed description and accompanying drawings, in which:

FIG. 8A is a schematic exploded view illustrating the combination of the piezoelectric actuator and the base of FIG. 5C;

DETAILED DESCRIPTION OF THE PREFERRED EMBODIMENT

The present disclosure will now be described more specifically with reference to the following embodiments. It is to be noted that the following descriptions of preferred embodiments of this invention are presented herein for purpose of illustration and description only. It is not intended to be exhaustive or to be limited to the precise form disclosed.

Figure 1A:
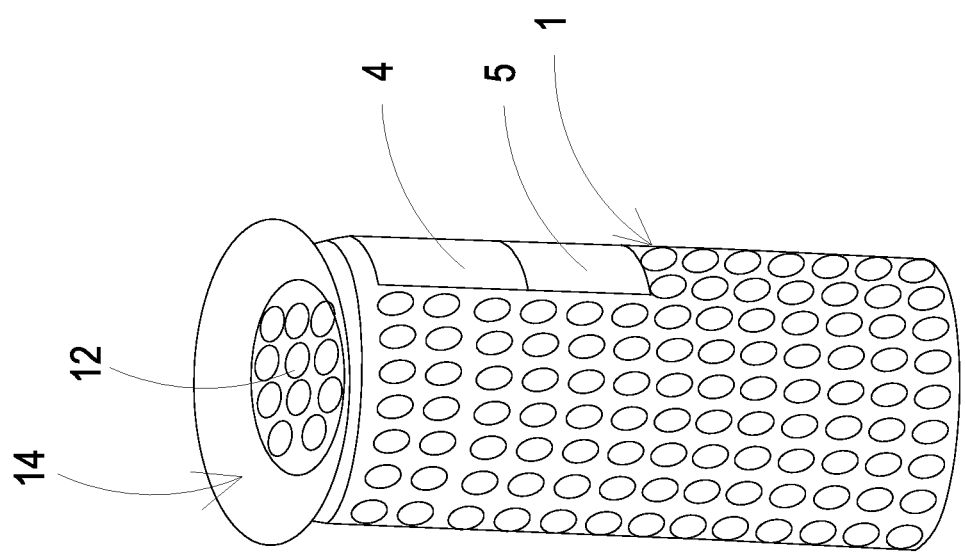
FIG. 1A is a schematic view illustrating a purification device for exercise environment according to an embodiment of the present disclosure.
Figure 2A:
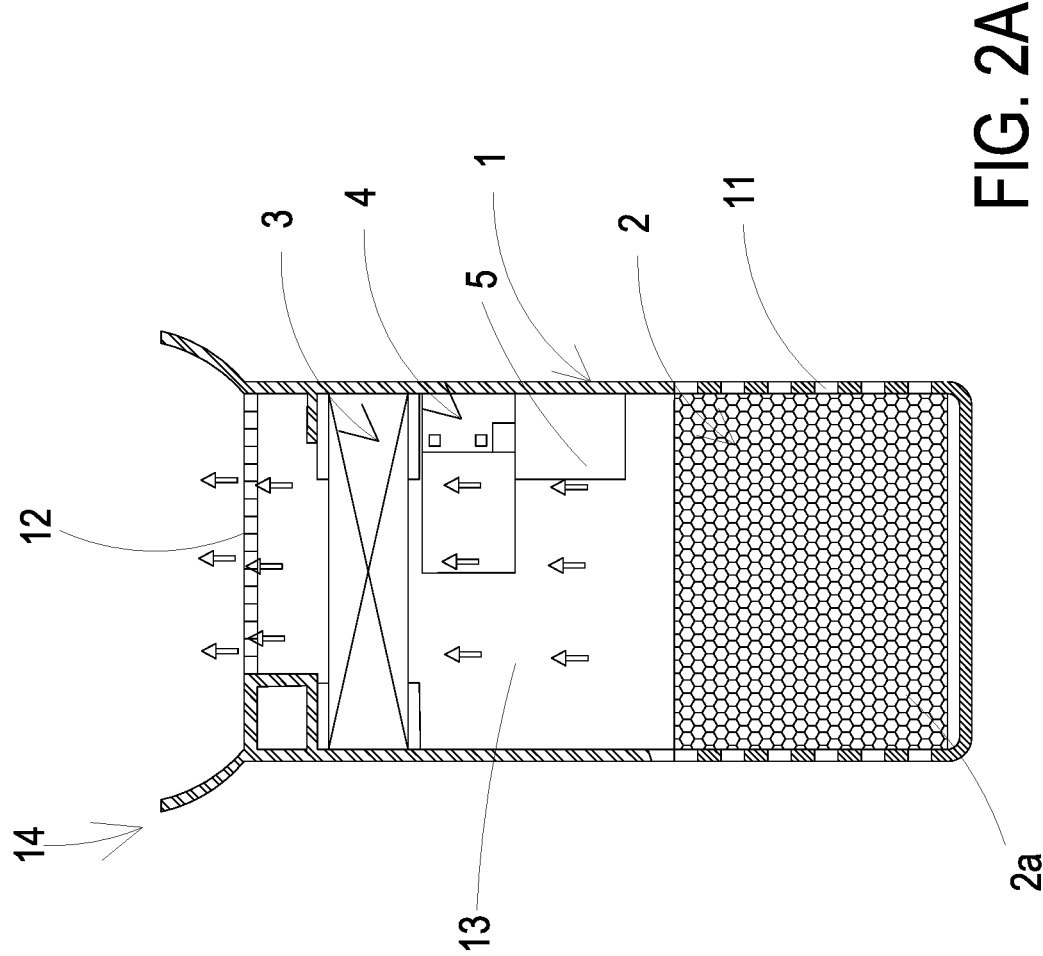
FIG. 2A is a cross-section view of the purification device for exercise environment of the present disclosure.

Please refer to FIGS. 1A and 2A. The present disclosure provides a purification device for exercise environment applied in an exercise environment and including a main body 1, a purification unit 2, a gas guider 3, a gas detection module 4 and a power unit 5. In the embodiment, the power unit 5 provides power for the purification unit 2, the gas guider 3 and the gas detection module 4 to start operation. The main body 1 includes at least one gas inlet 11 and at least one gas outlet 12. The purification unit 2 is disposed in the main body 1 for filtering a gas introduced into the main body 1 through the at least one gas inlet 11. The gas guider 3 disposed in the main body 1 is adjacent to the at least one gas outlet 12 for filtering and purifying the gas outside the main body 1 inhaled and flowed through the purification unit 2, so that a purified gas is filtered and discharged out through the at least one gas outlet 12. The gas detection module 4 is disposed in the main body 1 for detecting a particle concentration of suspended particles contained in the purified gas filtered through the purification unit 2. In the embodiment, the gas guider 3 is constantly controlled to operate and export a gas at an airflow rate within 3 minutes to reduce the particle concentration of the suspended particles contained in the purified gas to less than 0.75 μg/m$^3$, so as to provide the purified gas through safe filtration to an exerciser for breathing in the exercise environment.

In addition, the present disclosure provides purification device for exercise environment. How to apply the purification device to the exercise environment and perform a gas purification procedure is described as below.

Figure 1B:
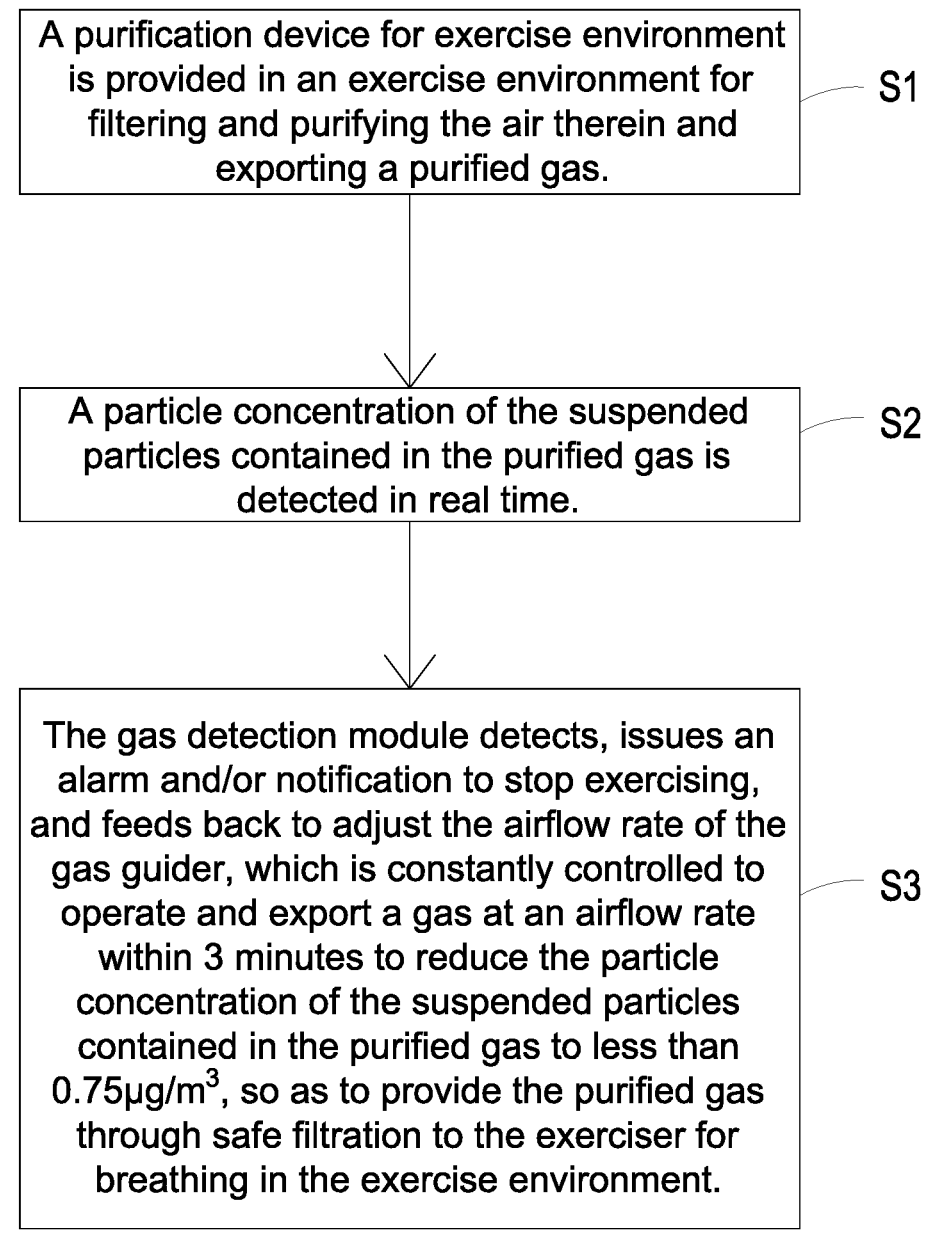
FIG. 1B schematically illustrates a processing method of performing an exercise environment purification by the purification device for exercise environment of the present disclosure.

Firstly, in one embodiment of the present disclosure as shown in FIG. 1B, a gas-purification processing method of the purification device for the exercise environment is provided, and includes the following steps as mentioned below.

Figure 14A:
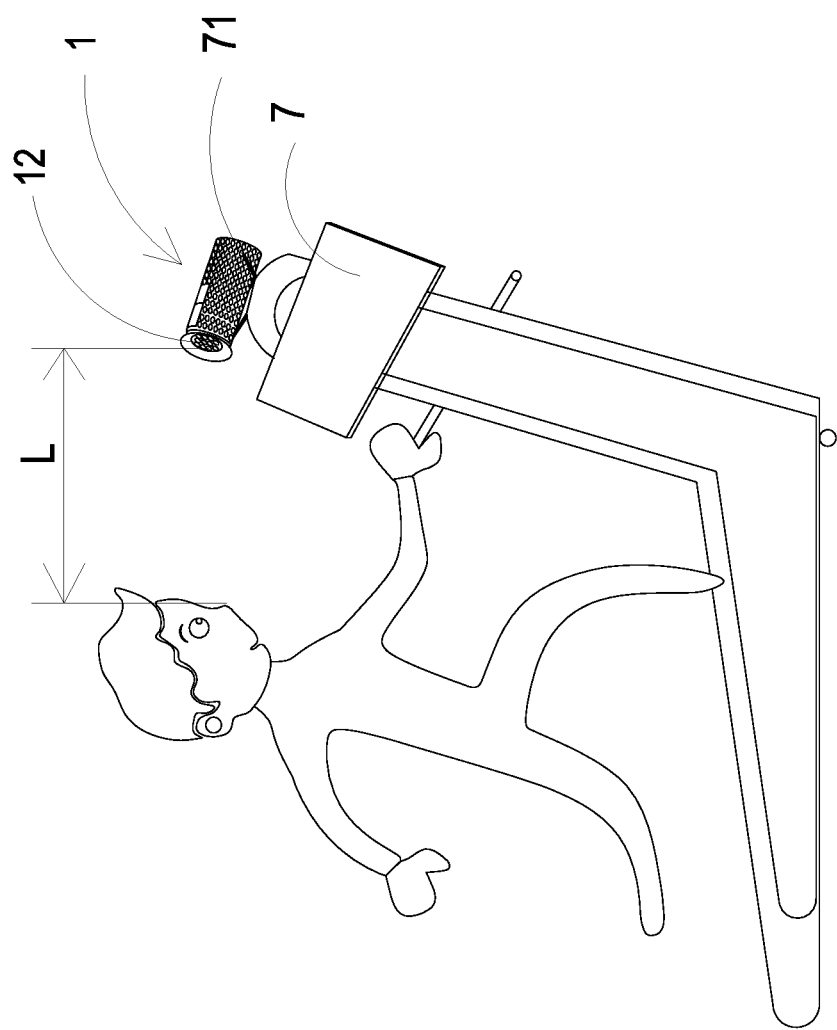
FIG. 14A is a schematic perspective view illustrating the purification device for exercise environment of the present disclosure, wherein the purification device for exercise environment is hanged on an exercise equipment in an exercise environment.

In a step S1, a purification device for exercise environment is provided in an exercise environment for filtering and purifying the air therein and exporting a purified gas. As shown in FIG. 2A, the purification device for exercise environment is formed by disposing the purification unit 2, the gas guider 3 and the gas detection module 4 in the main body 1 for filtering and purifying the gas and exporting a purified gas. In the embodiment, as shown in FIG. 1A and FIG. 14A, the main body 1 of the purification device for exercise environment is a directional gas-guiding device, which is fixedly combined with an exercise equipment by a fixed frame 71. Moreover, a directional guiding element 14 is disposed in the at least one gas outlet 12 of the main body 1, so that a purified gas that has been directional filtered can be discharged from the at least one gas outlet 12. In the embodiment, the at least one gas outlet 12 of the main body 1 maintains a breathing distance L from a breathing region around the nose of the exerciser, and the breathing distance L is ranged from 60 cm to 200 cm. The exercise equipment 7 is selected from the group consisting of a treadmill, an elliptical machine, a climber, an exercise bike, a flywheel, a recumbent board, a step machine and a rehabilitation machine. In this embodiment, the exercise equipment 7 is a treadmill.

In a step S2, a particle concentration of the suspended particles contained in the purified gas is detected in real time. As shown in FIG. 2A, the particle concentration of the suspended particles contained in the purified gas and filtered by the purification unit 2 is detected by the gas detection module 4 in real time.

Figure 5A:
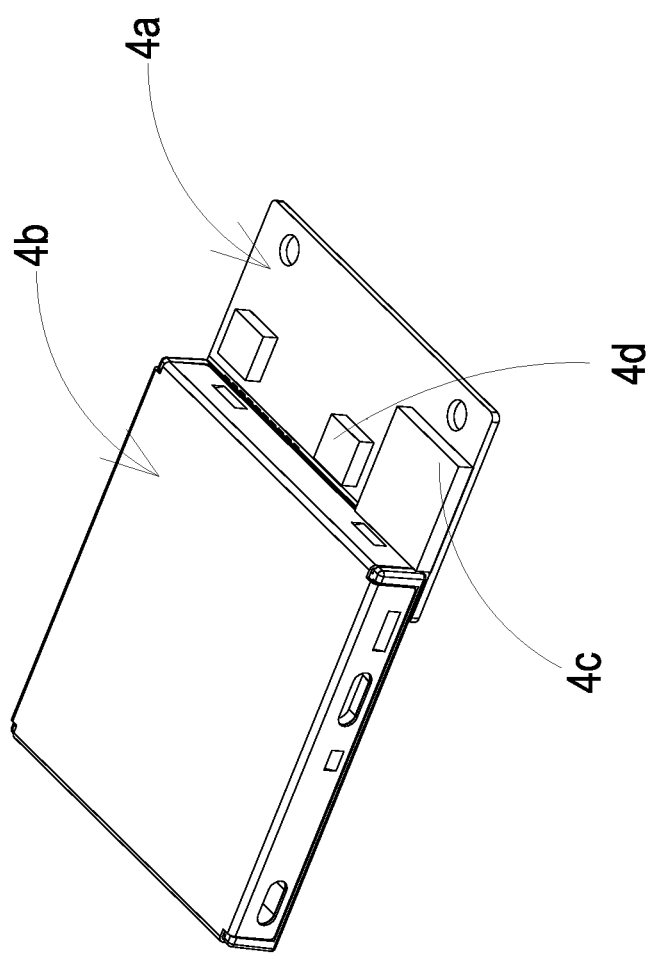
FIG. 5A is schematic exterior view illustrating a gas detection module of the purification device for exercise environment.
Figure 13:
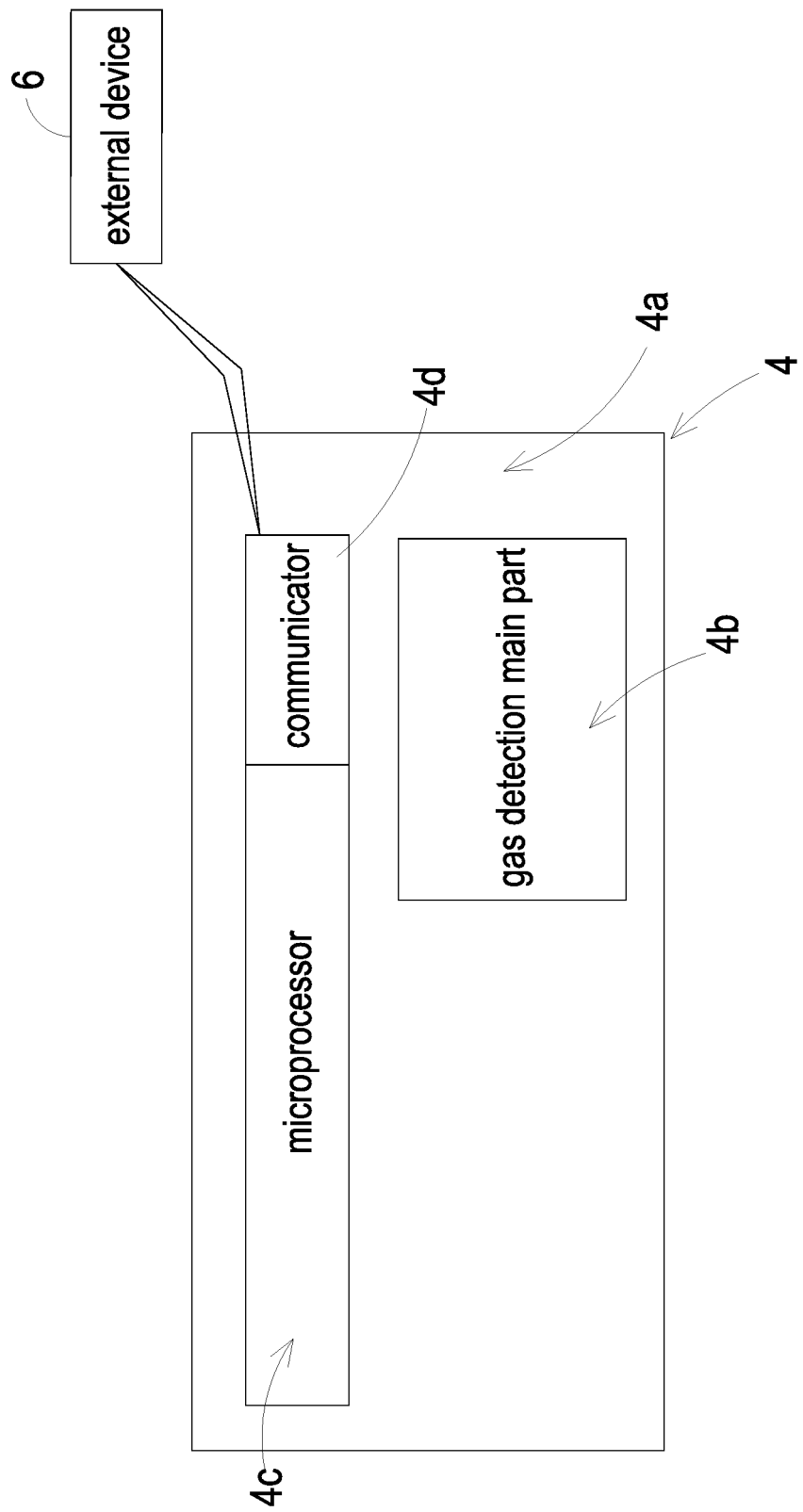
FIG. 13 is a block diagram illustrating a configuration of a controlling circuit board and the related components of the purification device for exercise environment of the present disclosure.
Figure 14B:
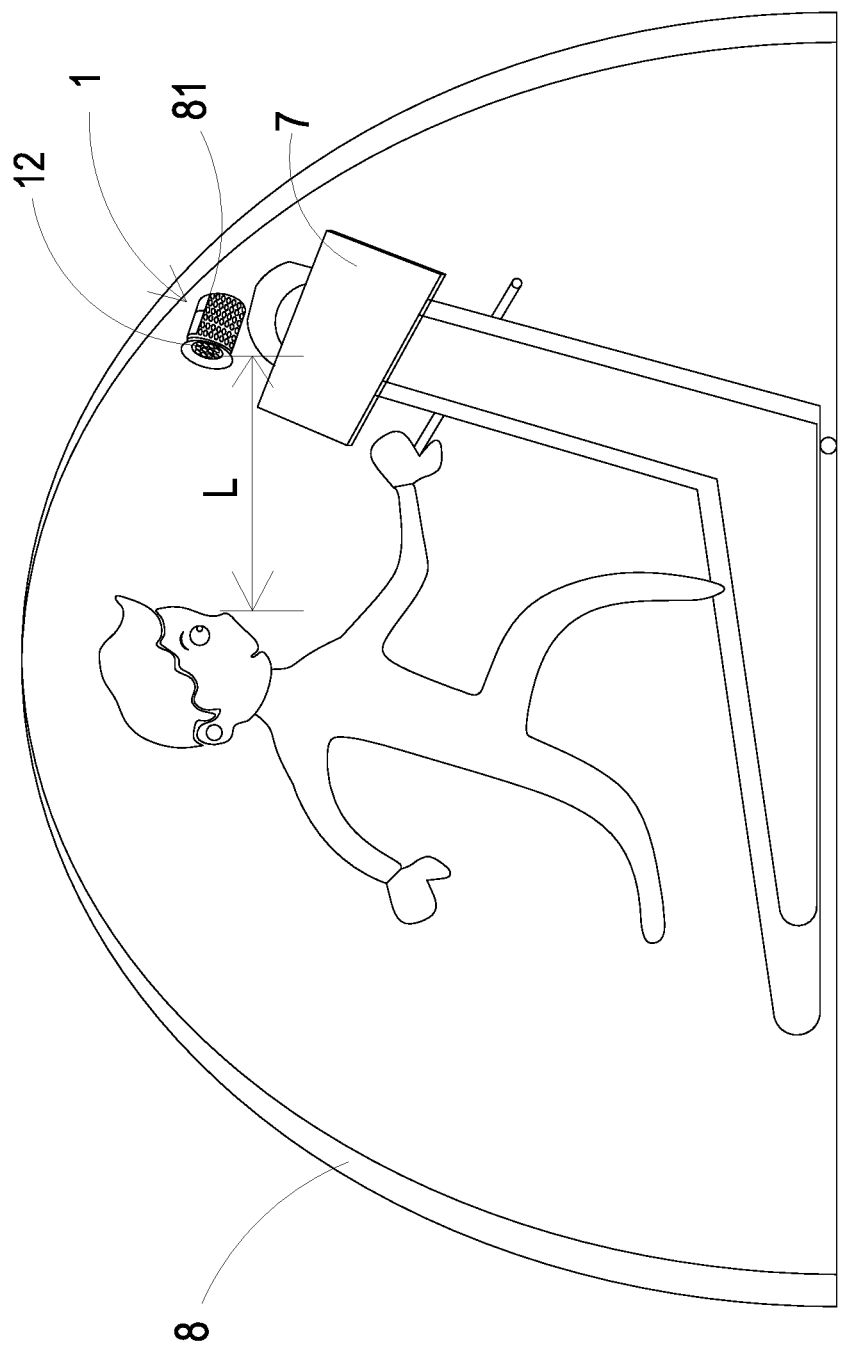
FIG. 14B is a schematic perspective view illustrating the purification device for exercise environment of the present disclosure, wherein the purification device for exercise environment is hanged on an isolation cover in the exercise environment.

In a step S3, the gas detection module 4 detects, issues an alarm and/or notification to stop exercising, and feeds back to adjust the airflow rate of the gas guider 3, which is constantly controlled to operate and export a gas at an airflow rate within 3 minutes to reduce the particle concentration of the suspended particles contained in the purified gas to less than 0.75 µg/m$^3$, so as to provide the purified gas through safe filtration to the exerciser for breathing in the exercise environment. In the embodiment, the gas detection module 4 detects the particle concentration of the suspended particles contained in the purified gas and set up a threshold of 0.75 µg/m$^3$. As shown in FIG. 5A and FIG. 13, the gas detection module 4 includes a controlling circuit board 4a, a gas detection main part 4b, a microprocessor 4c and a communicator 4d. In the embodiment, the gas detection main part 4b, the microprocessor 4c and the communicator 4d are integrally packaged on the controlling circuit board 4a and electrically connected to the controlling circuit board 4a. The microprocessor 4c receives a detection datum of the particle concentration of the suspended particles contained in the purified gas from the gas detection module 4 for calculating and processing, and controls to enable and/or disabled the operations of the gas guider 3 for filtering and purifying the gas. The communicator 4d transmits the detection datum of the particle concentration received from the microprocessor 4c to an external device 6, such as a mobile device, a smart watch, a wearable device, a computer or a cloud device, through a communication transmission, so that the external device 6 obtains the detection datum of the particle concentration of the purified gas for recording, issuing an alarm and/or notification to the exerciser reminding him to stop exercising, and feeding back to the purification device for exercise environment to adjust the airflow rate of the gas guider 3. When the particle concentration in the detection datum is higher than the set threshold of particle concentration (i.e., 0.75 µg/m$^3$), the external device 6 issues an alarm and/or notification and gives feedback to notify the purification device for exercise environment to adjust the airflow rate of the gas guider 3 and control the gas guider 3 to operate and export a gas continuously within 3 minutes, and the airflow rate exported by the gas guider 3 is at least 800 ft$^3$/min (cubic foot per minute, CFM.) to reduce the particle concentration of the suspended particles contained in the purified gas to less than 0.75 µg/m$^3$, so as to provide the purified gas by safe filtration to the exerciser for breathing in the exercise environment. Certainly, in another embodiment, as shown in FIG. 14B, the exercise environment further includes an isolation cover 8 for covering the exercise equipment 7 and the exerciser. Moreover, the isolation cover 8 has an opening 81 for the main body 1 to fix therein and penetrate through the isolation cover 8. The at least one gas inlet 11 of the main body 1 is located outside the isolation cover 8, and the at least one gas outlet 12 of the main body 1 is located inside the isolation cover 8. The at least one gas outlet 12 of the main body 1 maintains a breathing distance L from a breathing region around the nose of the exerciser, and the breathing distance L is ranged from 60 cm to 200 cm. In this way, the airflow rate exported by the gas guider 3 of the purification device for exercise environment is less than 800 ft$^3$/min and doesn't need for larger airflow rate. Inside the isolation cover 8, the purified gas provided by safe filtration is enough to provide the exerciser to breath in the exercise environment. Preferably but not exclusively, the external communication transmission of the communicator 4d may be a wired two-way communication transmission, such as a USB communication transmission, or a wireless communication transmission, such as Wi-Fi communication transmission, Bluetooth communication transmission, a radio frequency identification communication transmission, or a near field communication (NFC) transmission.

According to the above description, in the purification device for exercise environment of the present disclosure, the gas detection module 4 is utilized to monitor the air quality in the exercise environment around the exerciser in real time, and the purification unit 2 is utilized to provide a solution for purifying the air. In this way, the gas detection module 4 and the purification unit 2 combined with the gas guider 3 can export a gas at a specific airflow amount, so as to provide the purified gas by filtering of purification unit 2. In addition, the gas guider 3 constantly controls the exported airflow rate within 3 minutes to reduce the particle concentration of the suspended particles contained in the purified gas to less than 0.75 µg/m$^3$, so as to achieve the purification effect of safe filtration. Moreover, the gas detection module 4 is used to detect the breathing region around the nose of the exerciser in the exercise environment, so as to ensure that the purified gas is provided by safe filtration to the exerciser for breathing under an exercise state. The real-time information is available so that the exerciser in the exercise environment can be alarmed and notified to immediately take preventive measures such as stop exercising, or providing the isolation cover 8 for isolating the outside air and keep exercising in the isolation cover 8.

As shown in FIG. 2A, in the embodiment, the main body 1 further includes a gas-flow channel 13 disposed between the at least one gas inlet 11 and the at least one gas outlet 12. The gas guider 3 is disposed in the gas-flow channel 13 and located at a side of the purification unit 2 for filtering and purifying the gas, so that the gas is inhaled through the at least one gas inlet 11, flows through the purification unit 2 for filtering to provide the purified gas, and is discharged out through the at least one gas outlet 12. In this way, the gas detection module 4 can control the enablement and disablement of the gas guider 3. When the gas guider 3 is enabled, the gas outside the main body 1 is inhaled through the at least one gas inlet 11, flows through the purification unit 2 for filtering and purifying, and is discharged out through the at least one gas outlet 12, so as to provide the filtered and purified gas to the breathing region around the nose of exerciser for breathing.

The above-mentioned purification unit 2 disposed in the gas-flow channel 13 can be implemented in various embodiments. For example, as shown in FIG. 2A, the purification unit 2 includes a high efficiency particulate air (HEPA) filter screen 2a. When the gas is introduced into the gas-flow channel 13 by the gas guider 3, the gas is filtered through the HEPA filter screen 2a to adsorb the chemical smoke, bacteria, dust particles and pollen contained in the gas to achieve the effects of filtering and purifying the gas introduced into the main body 1. In some embodiments, the HEPA filter screen 2a is coated with a clean factor containing chlorine dioxide to inhibit viruses, bacteria, influenza A virus, influenza B virus, enterovirus or norovirus in the gas outside the main body 1. The inhibition rate reaches more than 99%. It is helpful of reducing the cross-infection of viruses. In other embodiments, the HEPA filter screen 2a is coated with an herbal protective layer extracted from ginkgo and Japanese rhus chinensis to form an herbal protective anti-allergic filter, so as to resist allergy effectively and destroy a surface protein of influenza virus, such as H1N1 influenza virus, in the gas introduced into the main body 1 and passing through HEPA filter screen 2a. In some other embodiments, the HEPA filter screen 2a is coated with a silver ion to inhibit viruses and bacteria in the gas introduced into the main body 1.

Figure 2B:
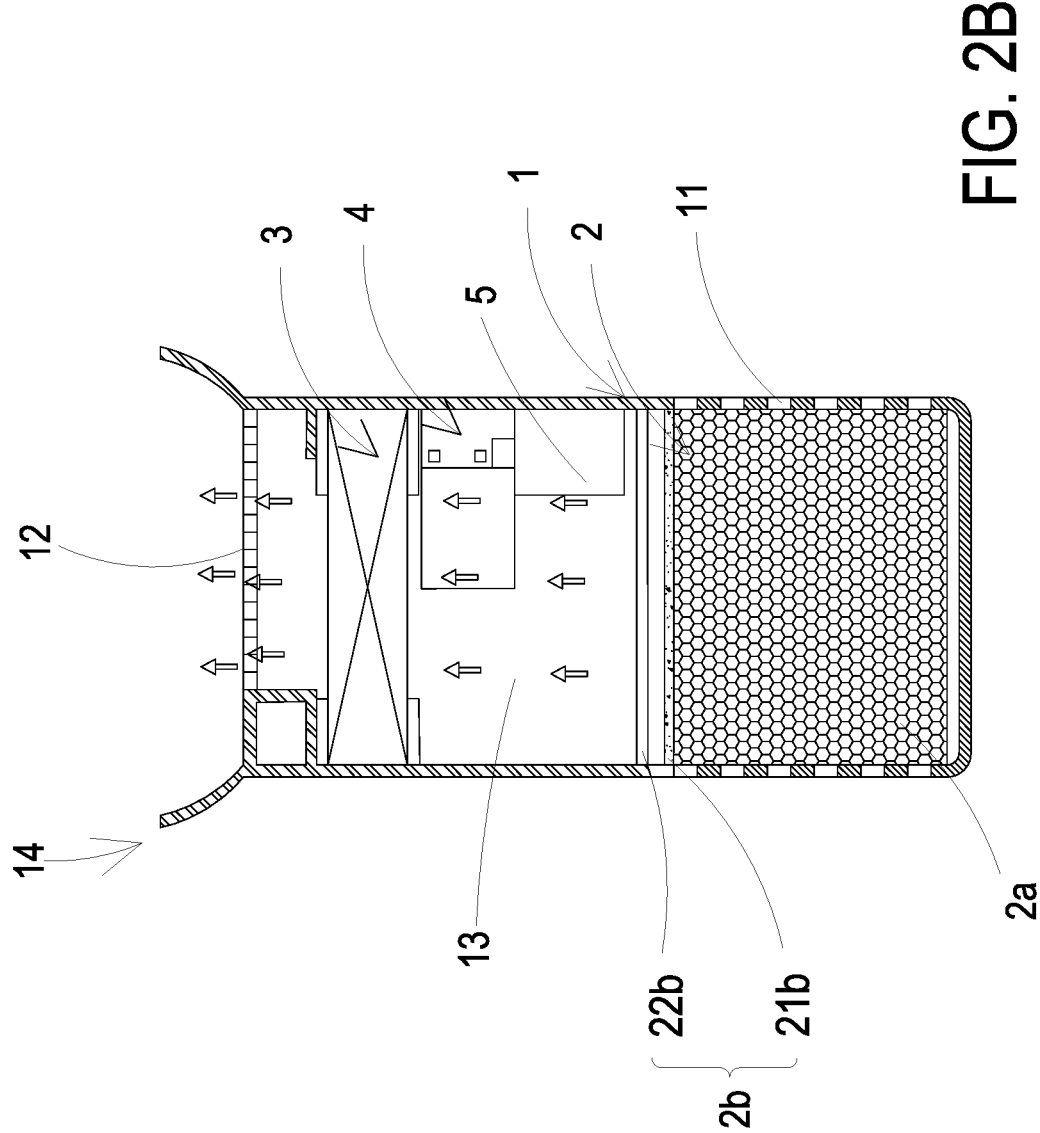
FIG. 2B is a cross-section view of a purification unit of FIG. 2A when the purification unit is formed by a high efficiency particulate air filter screen combined with a photocatalyst unit.

As shown in FIG. 2B, in the embodiment, the purification unit 2 includes a photo-catalyst unit 2b combined with the HEPA filter screen 2a. The photo-catalyst unit 2b includes a photo-catalyst 21b and an ultraviolet lamp 22b. The photo-catalyst 21b is irradiated with the ultraviolet lamp 22b to decompose the gas introduced into the main body 1 for filtering and purification, so as to purify the gas. In the embodiment, the photo-catalyst 21b and the ultraviolet lamp 22b are disposed in the gas-flow channel 13, respectively, and spaced apart from each other at a distance. In the embodiment, the gas outside the main body 1 is introduced into the gas-flow channel 13 by the gas guider 3, and the photo-catalyst 21b is irradiated by the ultraviolet lamp 22b to convert light energy into chemical energy, thereby decomposes harmful gases and disinfect bacteria contained in the gas, thereby achieving the effects of filtering and purification the introduced gas.

Figure 2C:
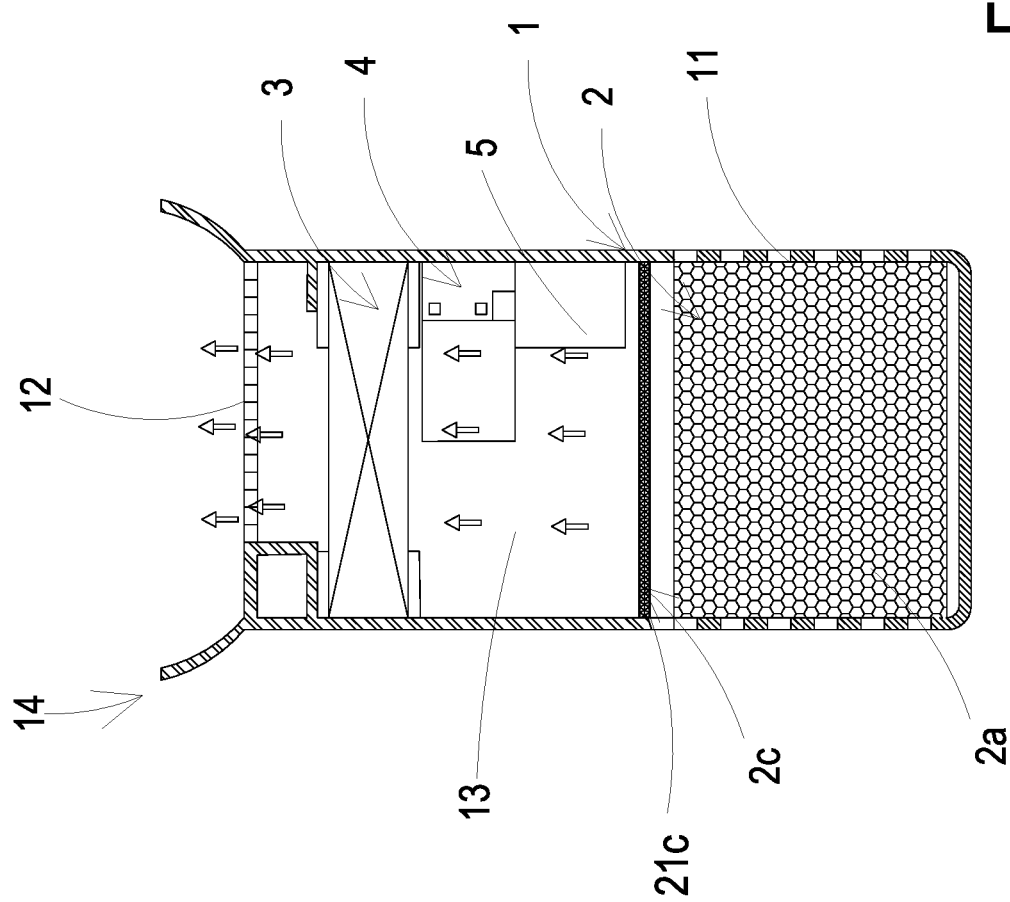
FIG. 2C is a cross-section view of a purification unit of FIG. 2A when the purification unit is formed by the high efficiency particulate air filter screen combined with a photoplasma unit.

As shown in FIG. 2C, in the embodiment, the purification unit 2 includes a photo-plasma unit 2c combined with the HEPA filter screen 2a. The photo-plasma unit 2c includes a nanometer irradiation tube 21c. The gas introduced into the main body 1 is irradiated by the nanometer irradiation tube 21c to decompose volatile organic gases contained in the gas and purify the gas. In the embodiment, the nanometer irradiation tube 21c is disposed in the gas-flow channel 13. When the gas outside the main body 1 is introduced into the gas-flow channel 13 by the gas guider 3, the gas is irradiated by the nanometer irradiation tube 21c, thereby decomposes oxygen molecules and water molecules contained in the gas into high oxidizing photo-plasma, which is an ion flow capable of destroying organic molecules. In that, volatile formaldehyde, volatile toluene and volatile organic (VOC) gases contained in the gas are decomposed into water and carbon dioxide, so as to achieve the effects of filtering and purifying gas.

Figure 2D:
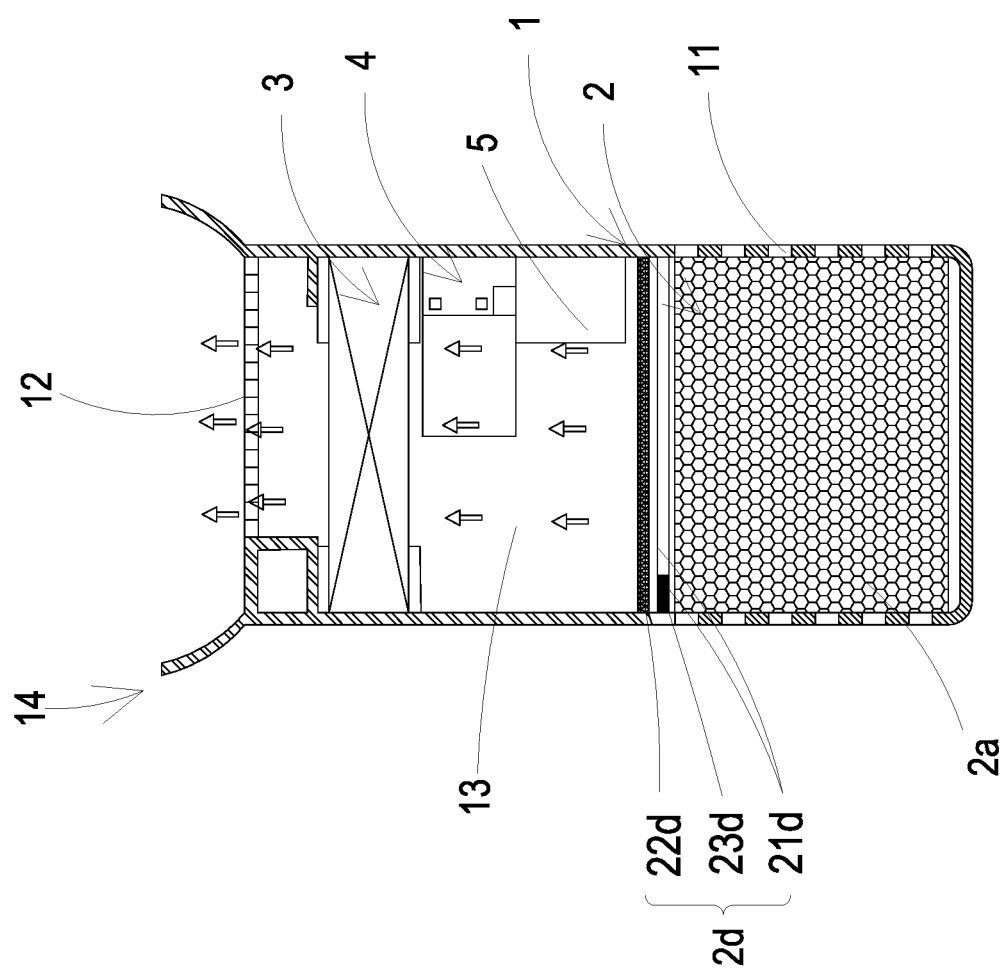
FIG. 2D is a cross-section view of a purification unit of FIG. 2A when the purification unit is formed by the high efficiency particulate air filter screen combined with a negative ionizer.

As shown in FIG. 2D, in the embodiment, the purification unit 2 includes a negative ionizer 2d combined with the HEPA filter screen 2a. The negative ionizer 2d includes at least one electrode wire 21d, at least one dust collecting plate 22d and a boost power supply device 23d. When a high voltage is discharged through the electrode wire 21d, the suspended particles contained in the gas introduced into the main body 1 are attached to the dust collecting plate 22d to purify the gas. In the embodiment, the at least one electrode wire 21d and the at least one dust collecting plate 22d are disposed within the gas-flow channel 13. As the at least one electrode wire 21d is provided with a high voltage by the boost power supply device 23d to discharge, the dust collecting plate 22d carries negative charge. When the gas outside the main body 1 is introduced into the gas-flow channel 13 by the gas guider 3, the at least one electrode wire 21d discharges to make the suspended particles in the gas to carry positive charge, therefore the suspended particles having positive charge are adhered to the dust collecting plate 22d carrying negative charges, so as to achieve the effects of filtering and purifying the introduced gas.

Figure 2E:
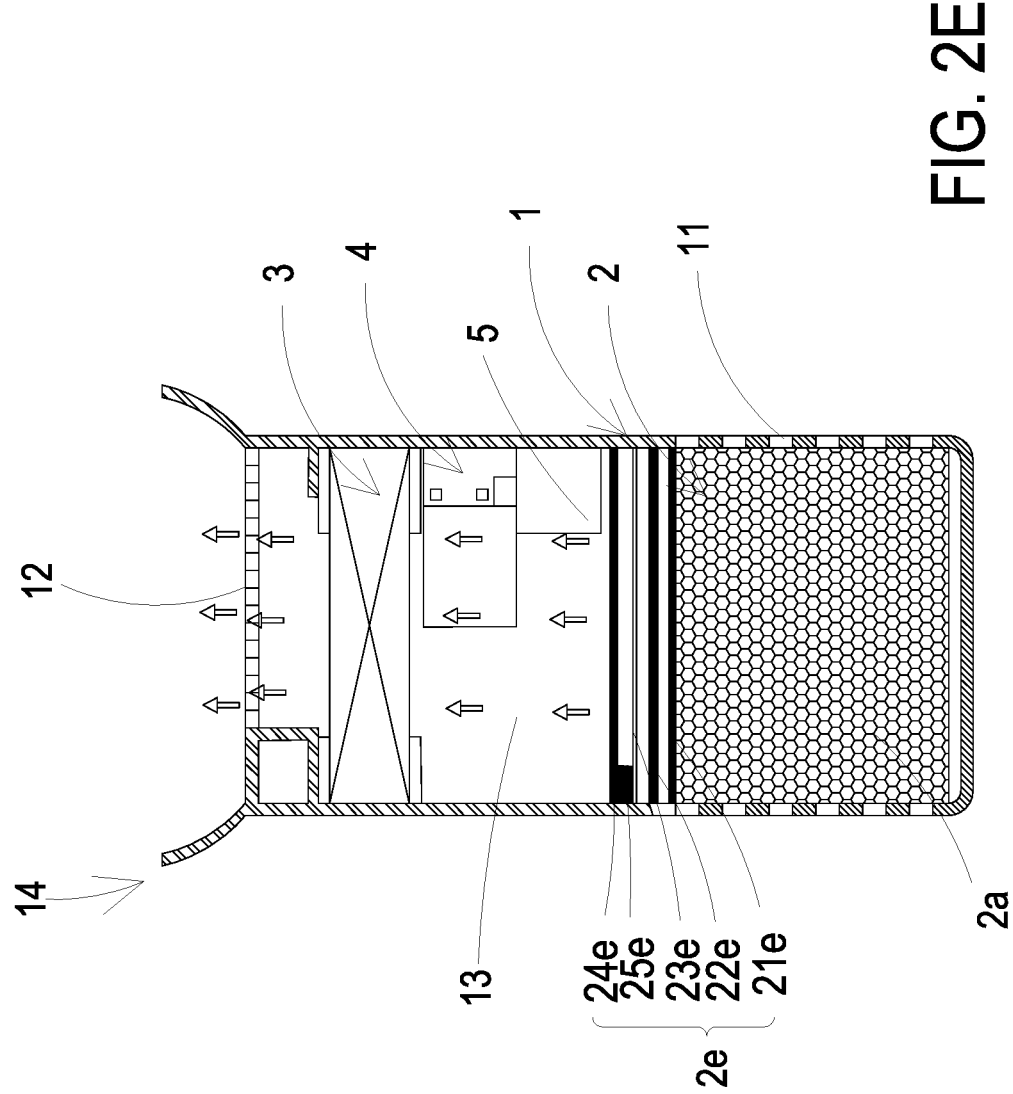
FIG. 2E is a cross-section view of a purification unit of FIG. 2A when the purification unit is formed by the high efficiency particulate air filter screen combined with a plasma ion unit.

As shown in FIG. 2E, in the embodiment, the purification unit 2 includes a plasma ion unit 2e combined with the HEPA filter screen 2a. The plasma ion unit 2e includes a first electric-field protection screen 21e, an adsorption filter screen 22e, a high-voltage discharge electrode 23e, a second electric-field protection screen 24e and a boost power supply device 25e. The boost power supply device 25e provides a high voltage to the high-voltage discharge electrode 23e to discharge and form a high-voltage plasma column with plasma ion, so as to decompose viruses or bacteria contained in the gas introduced into the main body 1 are by the plasma ion. In the embodiment, the first electric-field protection screen 21e, the adsorption filter screen 22e, the high-voltage discharge electrode 23e and the second electric-field protection screen 24e are disposed within the gas-flow channel 13. The adsorption filter screen 22e and the high-voltage discharge electrode 23e are located between the first electric-field protection screen 21e and the second electric-field protection screen 24e. As the high-voltage discharge electrode 23e is provided with a high voltage by the boost power supply device 25e to discharge, a high-voltage plasma column with plasma ion is formed. When the gas outside the main body 1 is introduced into the gas-guiding channel 13 by the gas guider 3, oxygen molecules and water molecules contained in the gas are decomposed into positive hydrogen ions ($H^+$) and negative oxygen ions ($O_2^-$) through the plasma ion. The substances attached with water around the ions are adhered on the surface of viruses and bacteria and converted into OH radicals with extremely strong oxidizing power, thereby removing the hydrogen (H) from the protein on the surface of viruses and bacteria, and decomposing (oxidizing) the protein, so as to filter the introduced gas and achieve the effects of filtering and purifying.

Preferably but not exclusively, the gas guider 3 is a fan, such as a vortex fan or a centrifugal fan. Alternatively, the gas guider 3 is an actuating pump 30, as shown in FIGS. 3A, 3B, 4A and 4B. In the embodiment, the actuating pump 30 includes a gas inlet plate 301, a resonance plate 302, a piezoelectric actuator 303, a first insulation plate 304, a conducting plate 305 and a second insulation plate 306, which are sequentially stacked on each other. In the embodiment, the gas inlet plate 301 includes at least one gas inlet aperture 301a, at least one convergence channel 301b and a convergence chamber 301c. The at least one gas inlet aperture 301a is disposed to inhale the gas outside the main body 1. The at least one gas inlet aperture 301a correspondingly penetrates through the gas inlet plate 301 into the at least one convergence channel 301b, and the at least one convergence channel 301b is converged into the convergence chamber 301c. In that, the gas inhaled through the at least one gas inlet aperture 301a is converged into the convergence chamber 301c. The number of the gas inlet apertures 301a is the same as the number of the convergence channels 301b. In the embodiment, the number of the gas inlet apertures 301a and the convergence channels 301b is exemplified by four, but not limited thereto. The four gas inlet apertures 301a penetrate through the gas inlet plate 301 into the four convergence channels 301b respectively, and the four convergence channels 301b converge to the convergence chamber 301c.

Figure 3A:
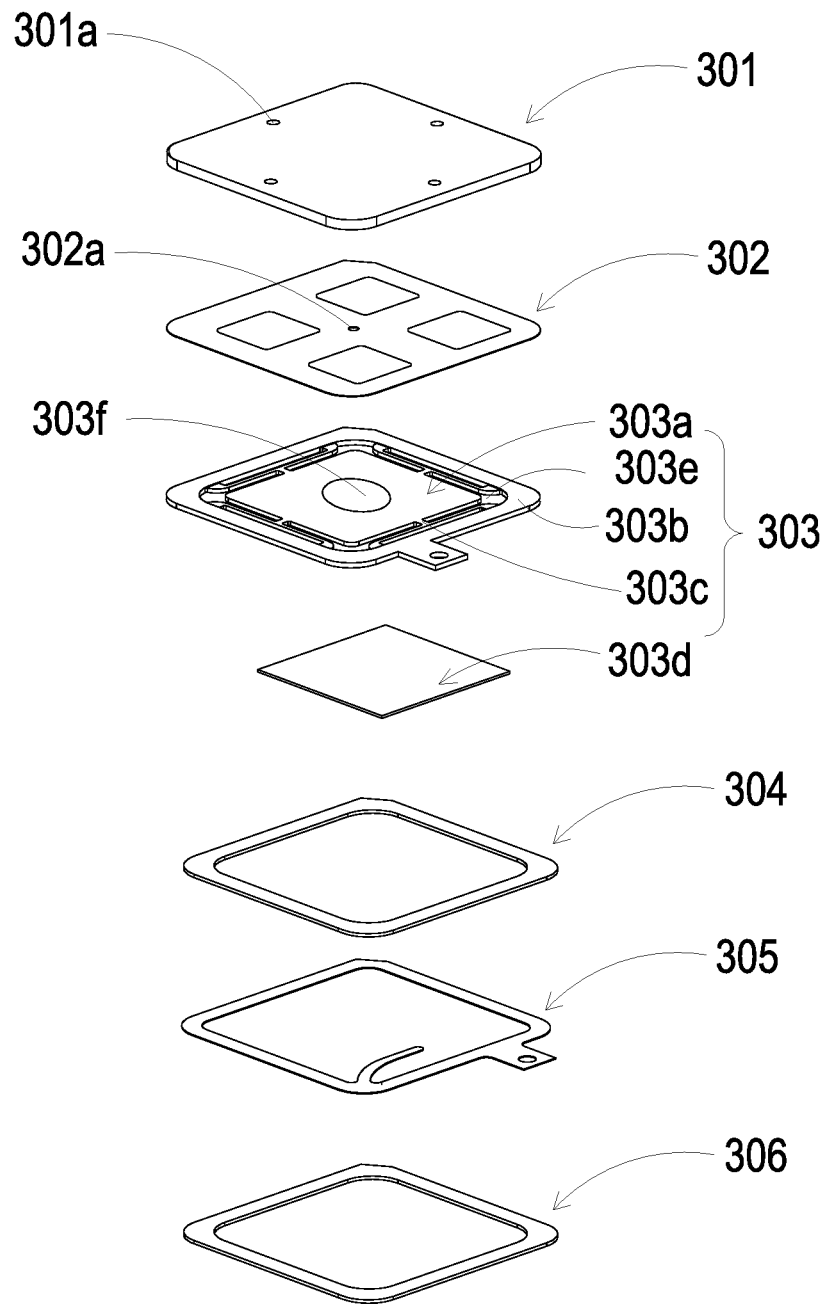
FIG. 3A is a schematic exploded front view of related components of a gas guider of the purification device for exercise environment of the present disclosure when the gas guider is an actuating pump.
Figure 3B:
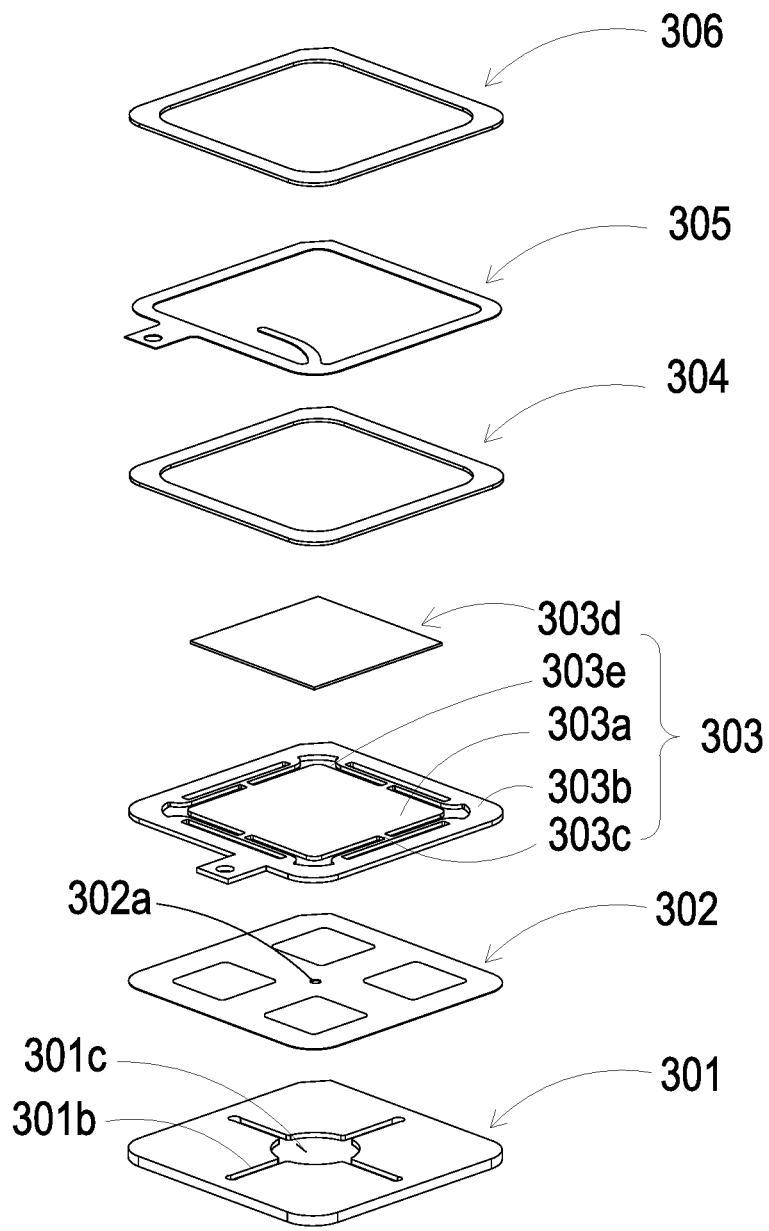
FIG. 3B is a schematic exploded rear view of related components of the gas guider of the purification device for exercise environment of the present disclosure when the gas guider is the actuating pump.
Figure 4A:
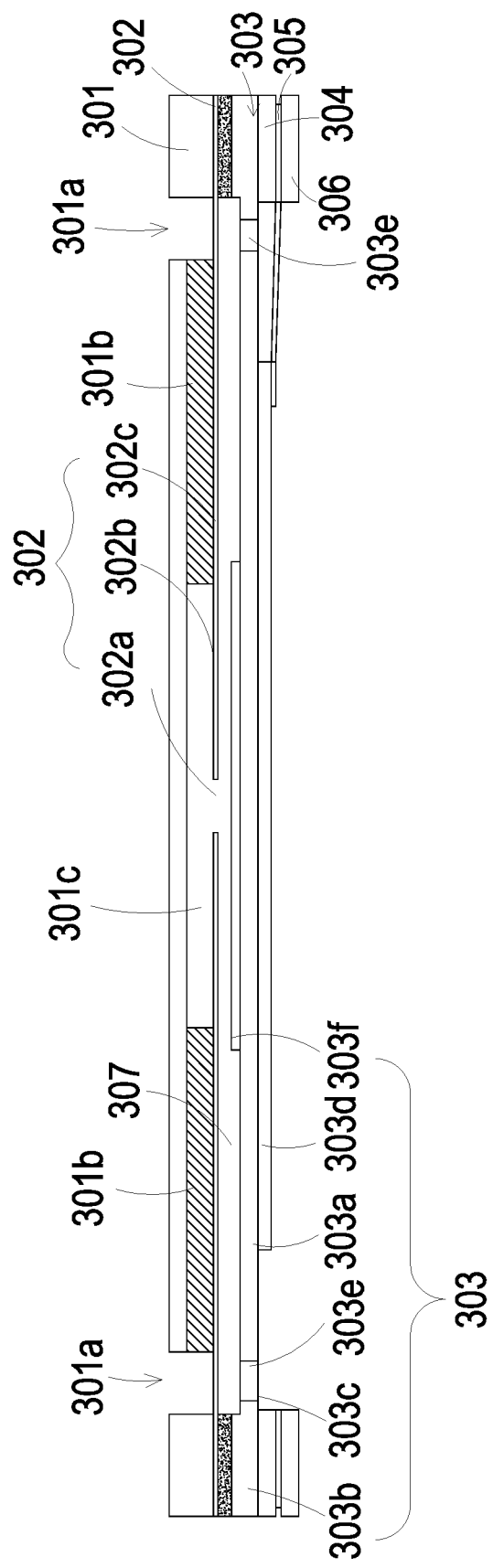
FIG. 4A is a cross-section view of the purification device for exercise environment of FIG. 3A when the related components of the gas guider of the purification device for exercise environment are assembled with each other and the gas guider is the actuating pump.

Please refer to FIGS. 3A, 3B and 4A. The resonance plate 302 is attached and assembled on the gas inlet plate 301. The resonance plate 302 has a central aperture 302a, a movable part 302b and a fixed part 302c. The central aperture 302a is located at a center of the resonance plate 302 and is corresponding in position to the convergence chamber 301c of the gas inlet plate 301. The movable part 302b surrounds the central aperture 302a and is corresponding in position to the convergence chamber 301c. The fixed part 302c is disposed around the periphery of the resonance plate 302 and firmly attached on the gas inlet plate 301.

Please refer to FIGS. 3A, 3B and 4A, again. The piezoelectric actuator 303 includes a suspension plate 303a, an outer frame 303b, at least one bracket 303c, a piezoelectric element 303d, at least one vacant space 303e and a bulge 303f. The suspension plate 303a is square-shaped because the square suspension plate 303a is more power-saving than the circular suspension plate. Generally, the consumed power of the capacitive load at the resonance frequency is positively related to the resonance frequency. Since the resonance frequency of the square suspension plate 303a is obviously lower than that of the circular suspension plate, the consumed power of the square suspension plate 303a is fewer. Therefore, the square suspension plate 303a in this embodiment is more effective in power-saving. In the embodiment, the outer frame 303b is disposed around the periphery of the suspension plate 303a. The at least one bracket 303c is connected between the suspension plate 303a and the outer frame 303b for elastically supporting the suspension plate 303a. The piezoelectric element 303d has a side, and a length of the side of the piezoelectric element 303d is less than or equal to that of the suspension plate 303a. The piezoelectric element 303d is attached on a surface of the suspension plate 303a. When a voltage is applied to the piezoelectric element 303d, the suspension plate 303a is driven to undergo the bending deformation. The at least one vacant space 303e is formed between the suspension plate 303a, the outer frame 303b and the at least one bracket 303c for allowing the gas to flow therethrough. The bulge 303f is formed on a surface of the suspension plate 303a opposite to the surface of the suspension plate 303a that the piezoelectric element 303d attached thereon. In this embodiment, the bulge 303f may be a convex structure integrally formed by using an etching process on the suspension plate 303a on a surface of the suspension plate 303a, which is opposite to the surface of the suspension plate 303a that attached on the piezoelectric element 303d attached thereon.

Please refer to FIGS. 3A, 3B and 4A. In the embodiment, the gas inlet plate 301, the resonance plate 302, the piezoelectric actuator 303, the first insulation plate 304, the conducting plate 305 and the second insulation plate 306 are stacked and assembled sequentially. A chamber space 307 is formed between the suspension plate 303a and the resonance plate 302, and the chamber space 307 can be formed by filling a gap between the resonance plate 302 and the outer frame 303b of the piezoelectric actuator 303 with a material, such as a conductive adhesive, but not limited thereto. Thus, a specific depth between the resonance plate 302 and the suspension plate 303a is maintained to form the chamber space 307 and allow the gas to pass rapidly. In addition, since a suitable distance between the resonance plate 302 and the suspension plate 303a is maintained, so that the contact interference therebetween is reduced and the noise generated thereby is largely reduced. In some other embodiments, the thickness of the conductive adhesive filled into the gap between the resonance plate 302 and the outer frame 303b of the piezoelectric actuator 303 is reduced by increasing the height of the outer frame 303b of the piezoelectric actuator 303. Therefore, the entire assembling structure of actuating pump 30 would not indirectly influence by the impact on the filling material resulting from the hot pressing temperature and the cooling temperature, so as to avoid the actual size of the formed chamber space 307 being influenced by the thermal expansion and cooling contraction of the filling material, i.e. conductive adhesive, but not limited thereto. In addition, since the transportation effect of the actuating pump 30 is affected by the chamber space 307, maintain a constant chamber space 307 is very important to provide a stable transportation efficiency of the actuating pump 30.

Figure 4B:
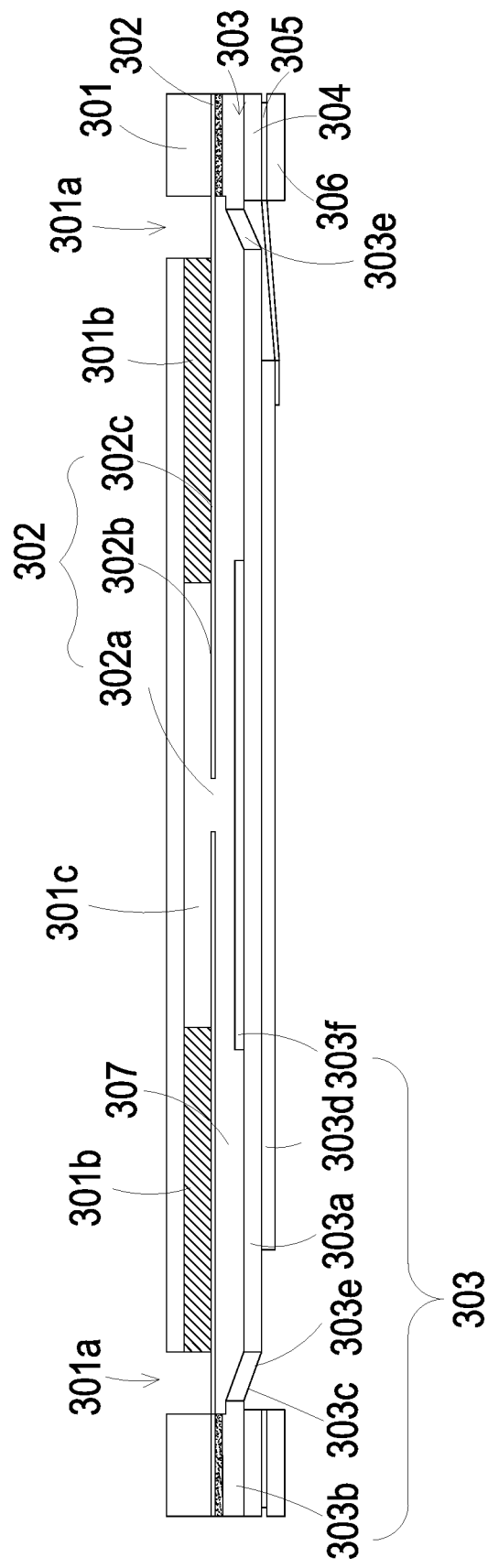
FIG. 4B is a cross-section view of the purification device for exercise environment of FIG. 3A when the related components of the gas guider of the purification device for exercise environment are assembled with each other and the gas guider is the actuating pump according to another embodiment of the present disclosure.

Please refer to FIG. 4B, in some other embodiments of the piezoelectric actuator 303, the suspension plate 303a is formed by stamping to make it extend outwardly a distance. The extended distance can be adjusted through the at least one bracket 303c formed between the suspension plate 303a and the outer frame 303b. Consequently, the surface of the bulge 303f disposed on the suspension plate 303a and the surface of the outer frame 303b are non-coplanar. Through applying small amount of filling materials, such as a conductive adhesive, to the coupling surface of the outer frame 303b, the piezoelectric actuator 303 is attached to the fixed part 302c of the resonance plate 302 by hot pressing, thereby assembling the piezoelectric actuator 303 and the resonance plate 302 in combination. Thus, the structure of the chamber space 307 is improved by directly stamping the suspension plate 303a of the piezoelectric actuator 303 described above. In this way, the required chamber space 307 can be obtained by adjusting the stamping distance of the suspension plate 303a of the piezoelectric actuator 303, thereby simplifying the structural design of the chamber space 307, and achieving the advantages of simplifying the manufacturing process and shortening the processing time. In addition, the first insulation plate 304, the conducting plate 305 and the second insulation plate 306 are all thin frame-shaped sheets, but are not limited thereto, and are sequentially stacked on the piezoelectric actuator 303 to complete the entire structure of actuating pump 30.

Figure 4C:
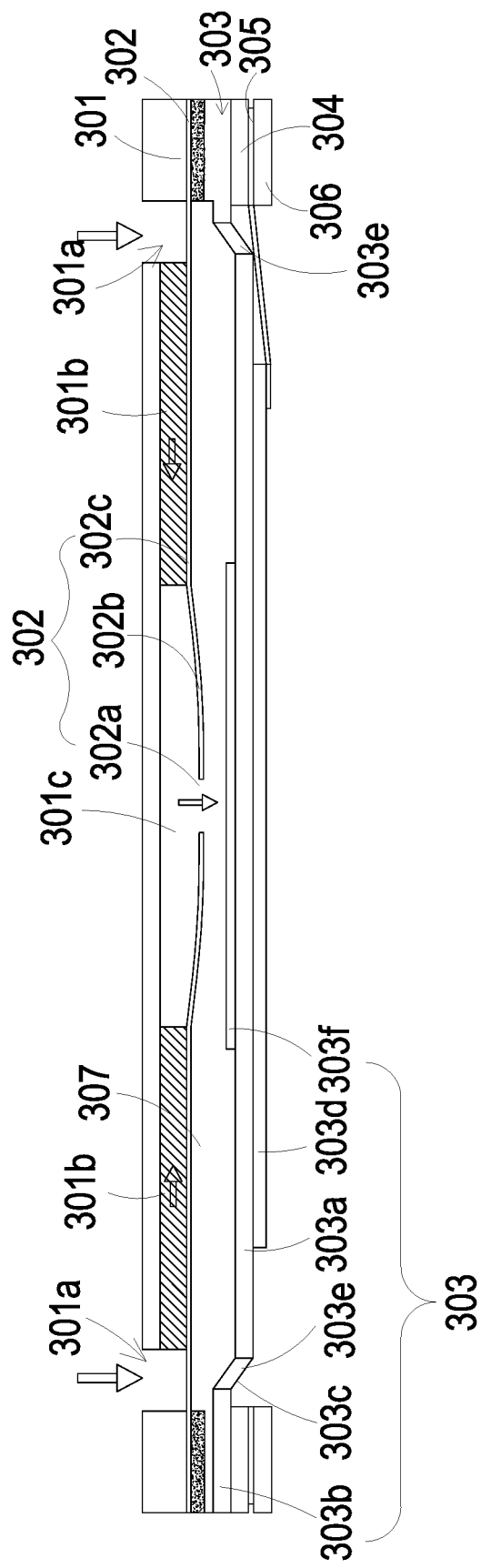
FIG. 4C to 4E schematically illustrates the operation steps of the actuating pump of FIG. 4A.
Figure 4D:
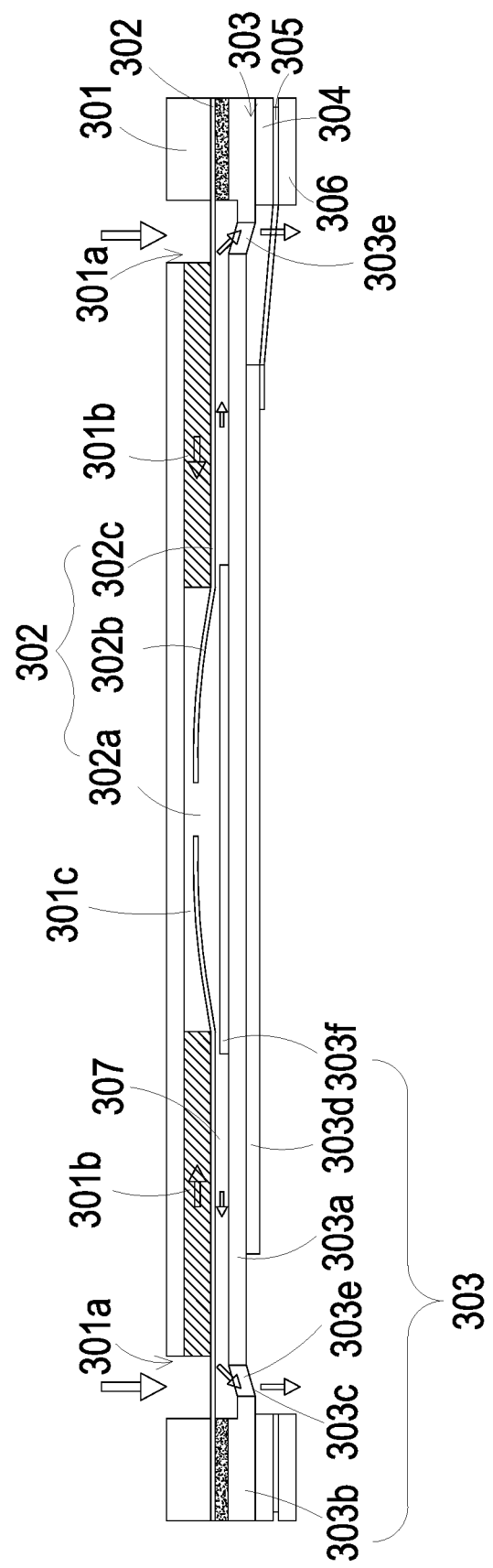
Figure 4E:
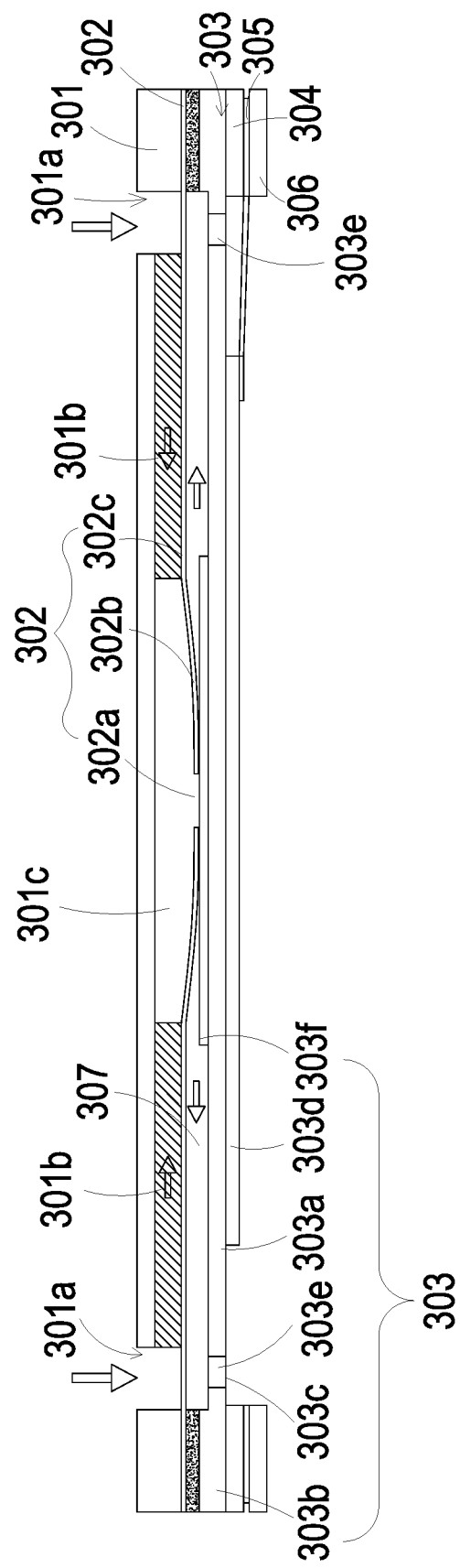

In order to understand the operation steps of the actuating pump 30, please refer to FIGS. 4C to 4E. Please refer to FIG. 4C, the piezoelectric element 303d of the piezoelectric actuator 303 is deformed after a voltage is applied thereto, the suspension plate 303a is driven to displace downwardly. In that, the volume of the chamber space 307 is increased, a negative pressure is generated in the chamber space 307, and the gas in the convergence chamber 301c is introduced into the chamber space 307. At the same time, the resonance plate 302 is displaced downwardly and synchronously in resonance with the suspension plate 303a. Thereby, the volume of the convergence chamber 301c is increased. Since the gas in the convergence chamber 301c is introduced into the chamber space 307, the convergence chamber 301c is also in a negative pressure state, and therefore the gas is sucked into the convergence chamber 301c through the gas inlet apertures 301a and the convergence channels 301b. Then, as shown in FIG. 4D, the piezoelectric element 303d drives the suspension plate 303a to displace upwardly to compress the chamber space 307. Similarly, the resonance plate 302 is actuated in resonance with the suspension plate 303a and is displaced upwardly. Thus, the gas in the chamber space 307 is further transported downwardly to pass through the vacant spaces 303e, and thereby achieving the effect of gas transportation. Finally, as shown in FIG. 4E, when the suspension plate 303a is driven and return to an initial state, the resonance plate 302 is also driven to displace downwardly due to inertia. In that, the resonance plate 302 pushes the gas in the chamber space 307 toward the vacant spaces 303e, and increases the volume of the convergence chamber 301c. Thus, the gas can continuously pass through the gas inlet apertures 301a and the convergence channels 301b, and then converged in the convergence chamber 301c. By repeating the operation steps illustrated in FIGS. 4C to 4E continuously, the actuating pump 30 can continuously transport the gas at high speed. The gas enters the gas inlet apertures 301a, flows through a flow path formed by the gas inlet plate 301 and the resonance plate 302 and generates a pressure gradient, and then transported downwardly through the vacant spaces 303e, so as to complete the gas transporting operation of the actuating pump 30.

Please refer to FIG. 5A to FIG. 5C, FIG. 6A to FIG. 6B, FIG. 7, FIG. 8A to FIG. 8B and FIG. 13. In the embodiment, the gas detection module 4 includes a controlling circuit board 4a, a gas detection main part 4b, a microprocessor 4c and a communicator 4d. The gas detection main part 4b, the microprocessor 4c and the communicator 4d are integrally packaged on the controlling circuit board 4a and electrically connected to the controlling circuit board 4a. The microprocessor 4c receives a detection datum of the particle concentration of the suspended particles contained in the purified gas for calculating and processing, and controls to enable and/or disabled the operations of the gas guider 3 for purifying the gas. The communicator 4d transmits the detection datum of the particle concentration received from the microprocessor 4c to an external device 6 through a communication transmission.

Figure 11A:
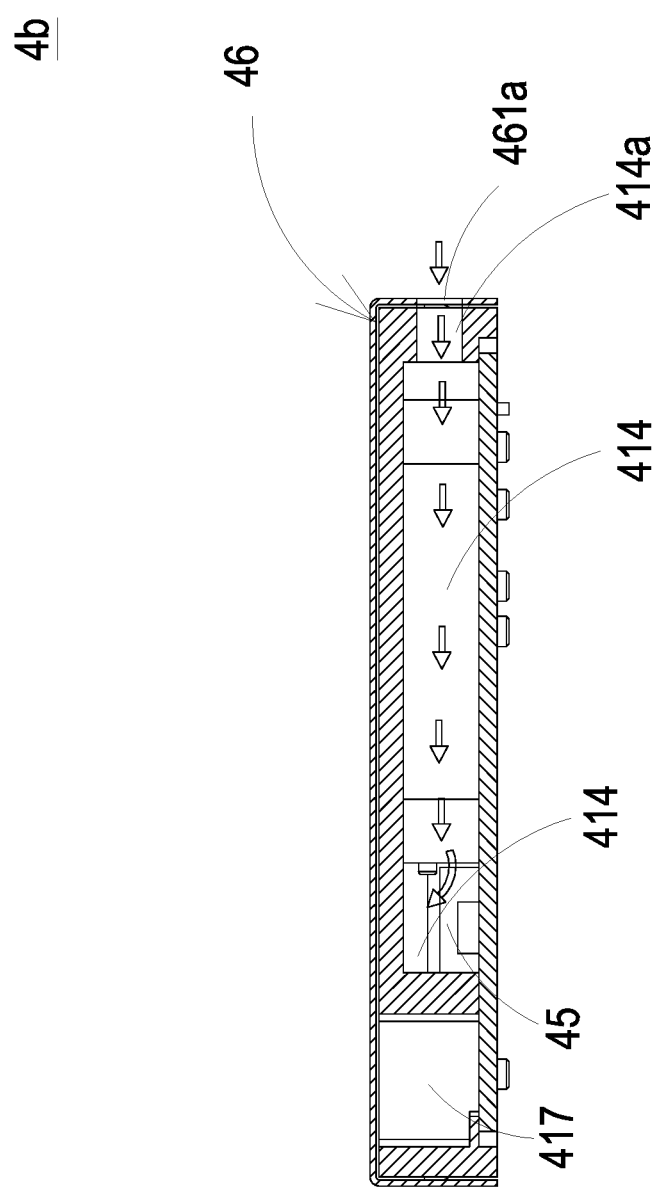
FIGS. 11A to 11C are cross-section views illustrating gas flowing paths of the gas detection main part of FIG. 5B from different angles.

As shown in FIG. 5A to FIG. 5C, FIG. 6A to FIG. 6B, FIG. 7, FIG. 8A to FIG. 8B, FIG. 9A to FIG. 9B and FIG. 11A to FIG. 11C, in the embodiment, the gas detection main part 4b includes a base 41, a piezoelectric-actuated element 42, a driving circuit board 43, a laser component 44, a particulate sensor 45 and an outer cover 46. The base 41 includes a first surface 411, a second surface 412, a laser loading region 413, a gas-inlet groove 414, a gas-guiding-component loading region 415 and a gas-outlet groove 416. In the embodiment, the first surface 411 and the second surface 412 are two surfaces opposite to each other. In the embodiment, the laser loading region 413 is hollowed out from the first surface 411 to the second surface 412. The gas-inlet groove 414 is concavely formed from the second surface 412 and disposed adjacent to the laser loading region 413. The gas-inlet groove 414 includes a gas-inlet 414a and two lateral walls. The gas-inlet 414a is in communication with an environment outside the base 41, and is corresponding in position to an inlet opening 461a of the outer cover 46. A transparent window 414b is opened on the two lateral walls and is in communication with the laser loading region 413. Therefore, the first surface 411 of the base 41 is covered and attached by the outer cover 46, and the second surface 412 is covered and attached by the driving circuit board 43. Thus, the gas-inlet groove 414 defines a gas-inlet path, as shown in FIG. 7 and FIG. 11A.

Figure 6A:
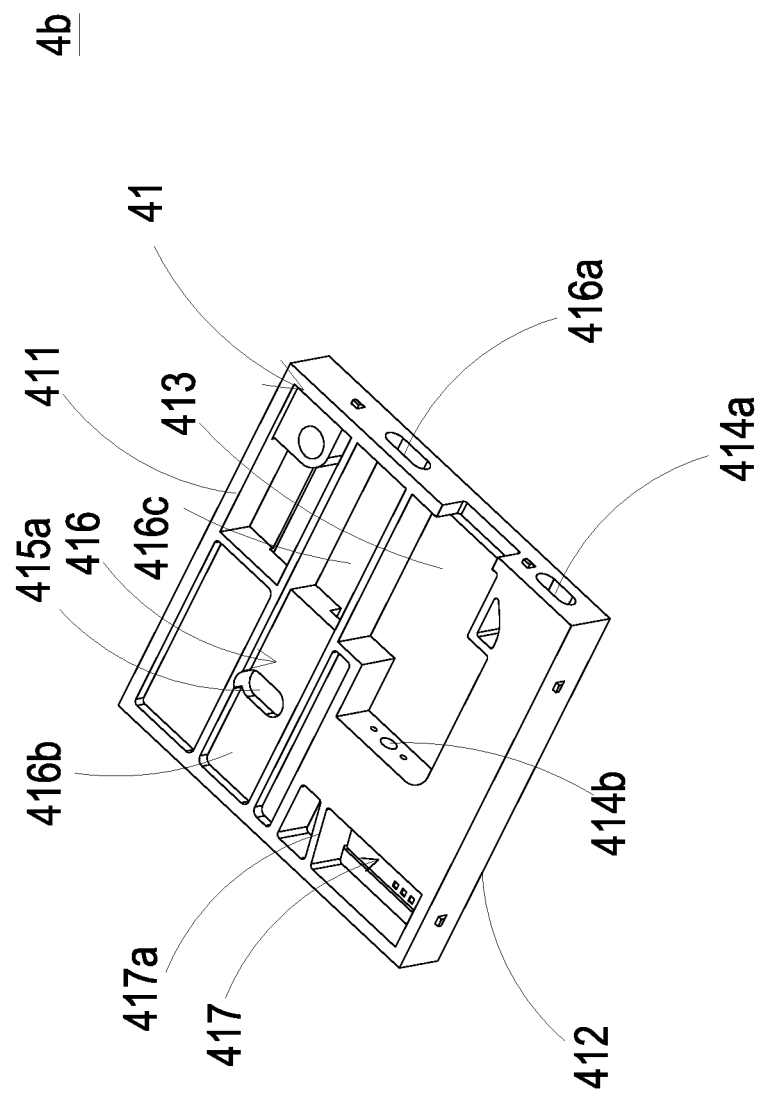
FIG. 6A is a schematic perspective front view illustrating a base of the gas detection main part of FIG. 5C.
Figure 6B:
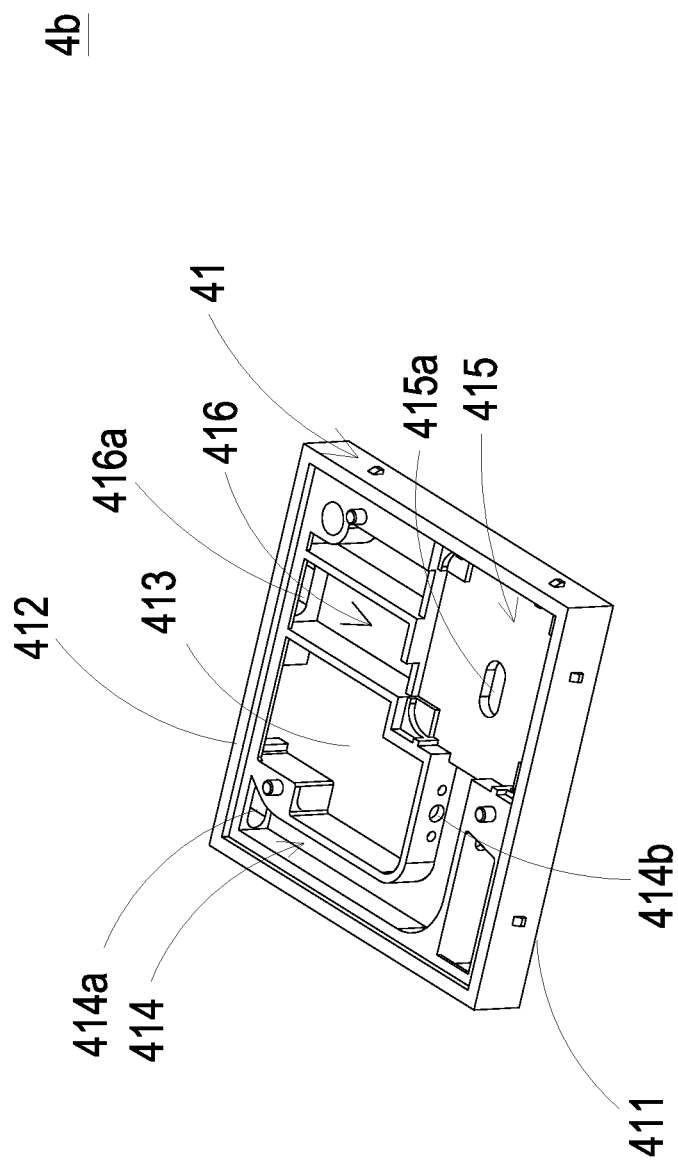
FIG. 6B is a schematic perspective rear view illustrating the base of the gas detection main part of FIG. 5C.
Figure 11B:
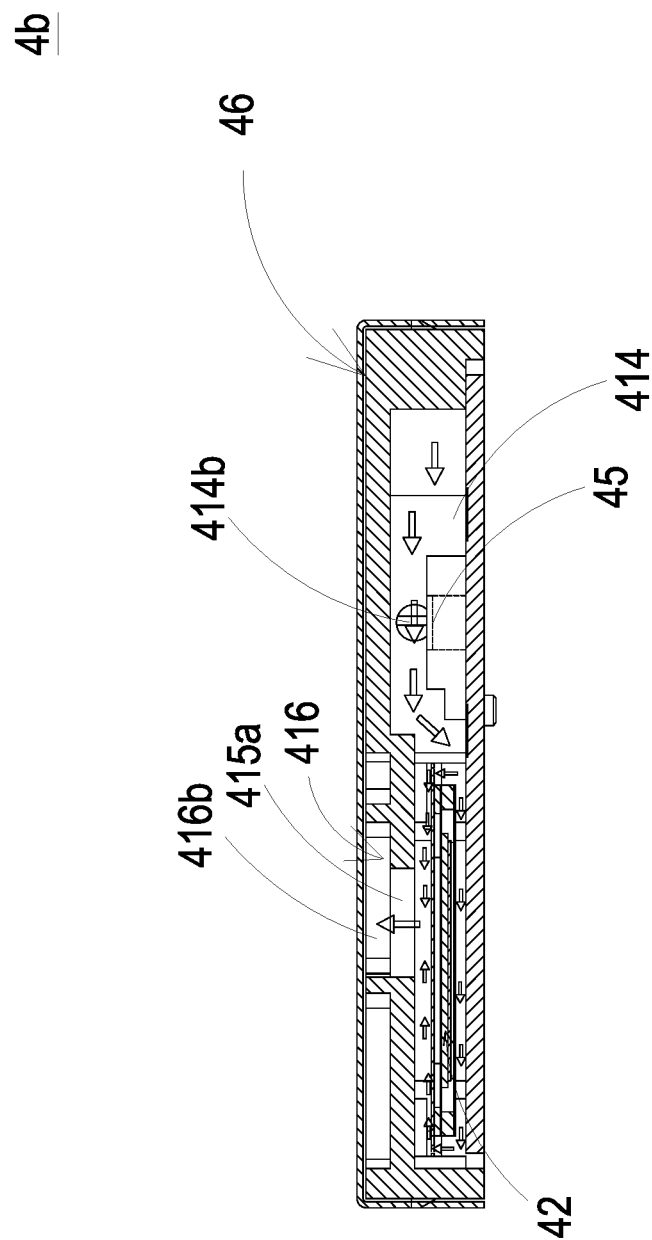
Figure 11C:
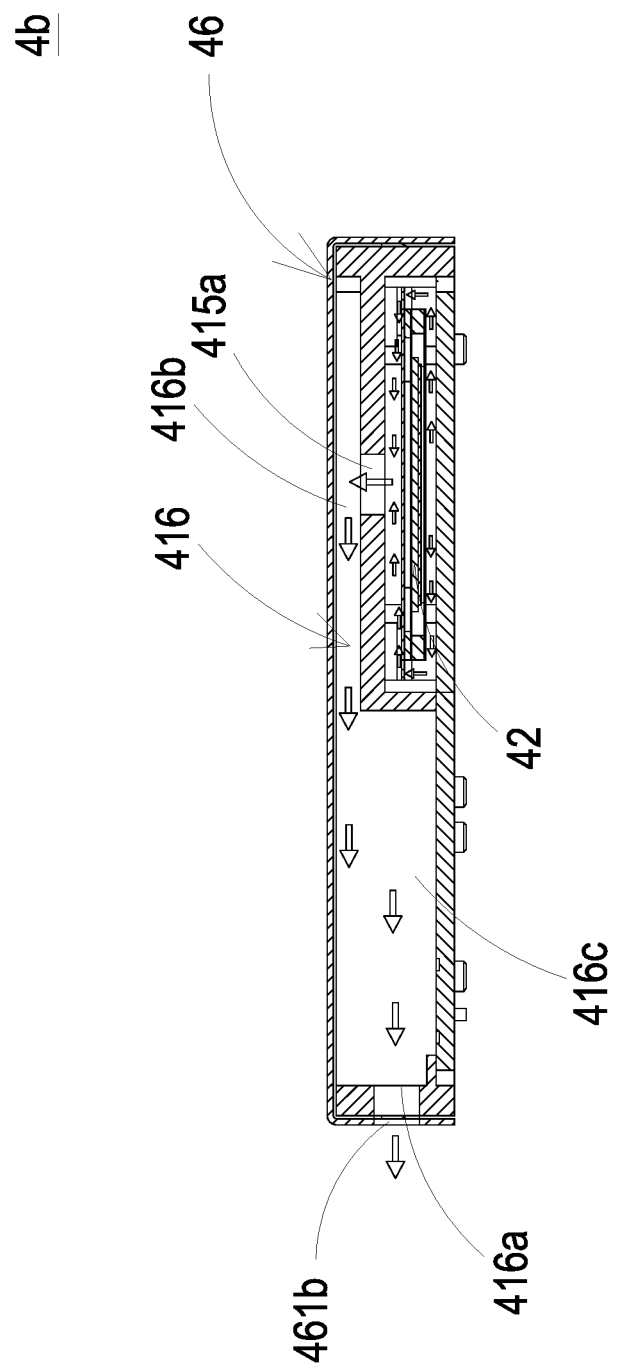

Please refer to FIGS. 6A to 6B. In the embodiment, the gas-guiding-component loading region 415 is concavely formed from the second surface 412 and in communication with the gas-inlet groove 414. A ventilation hole 415a penetrates a bottom surface of the gas-guiding-component loading region 415. In the embodiment, the gas-outlet groove 416 includes a gas-outlet 416a, and the gas-outlet 416a is spatially corresponding to the outlet opening 461b of the outer cover 46. The gas-outlet groove 416 includes a first section 416b and a second section 416c. The first section 416b is concavely formed on a region of the first surface 411 spatially corresponding to a vertical projection area of the gas-guiding-component loading region 415. The second section 416c is hollowed out from the first surface 411 to the second surface 412 in a region where the first surface 411 is not aligned with the vertical projection area of the gas-guiding-component loading region 415 and extended therefrom. The first section 416b and the second section 416c are connected to form a stepped structure. Moreover, the first section 416b of the gas-outlet groove 416 is in communication with the ventilation hole 415a of the gas-guiding-component loading region 415, and the second section 416c of the gas-outlet groove 416 is in communication with the gas-outlet 416a. In that, when first surface 411 of the base 41 is attached and covered by the outer cover 46, and the second surface 412 of the base 41 is attached and covered by the driving circuit board 43, such that the gas-outlet groove 416 and the driving circuit board 43 defines a gas-outlet path collaboratively, as shown in FIG. 7 and FIG. 11C.

Figure 5B:
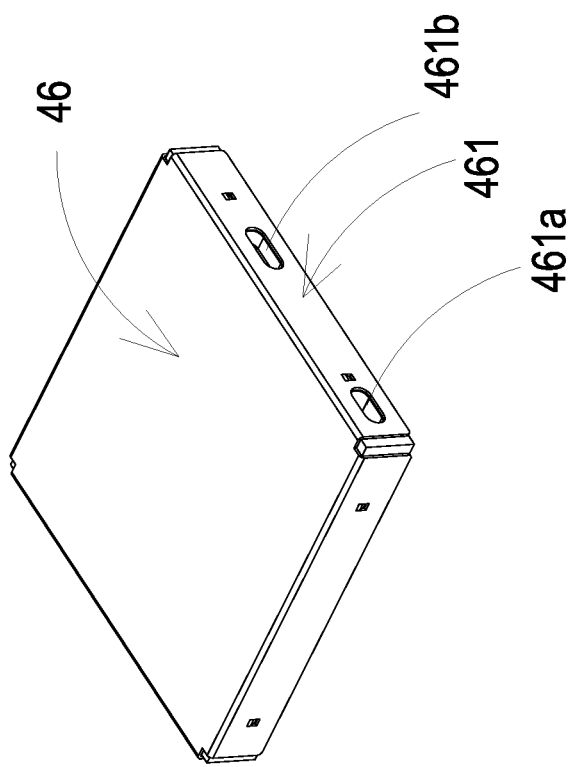
FIG. 5B is schematic exterior view illustrating a gas detection main part of the gas detection module of FIG. 5A.
Figure 5C:
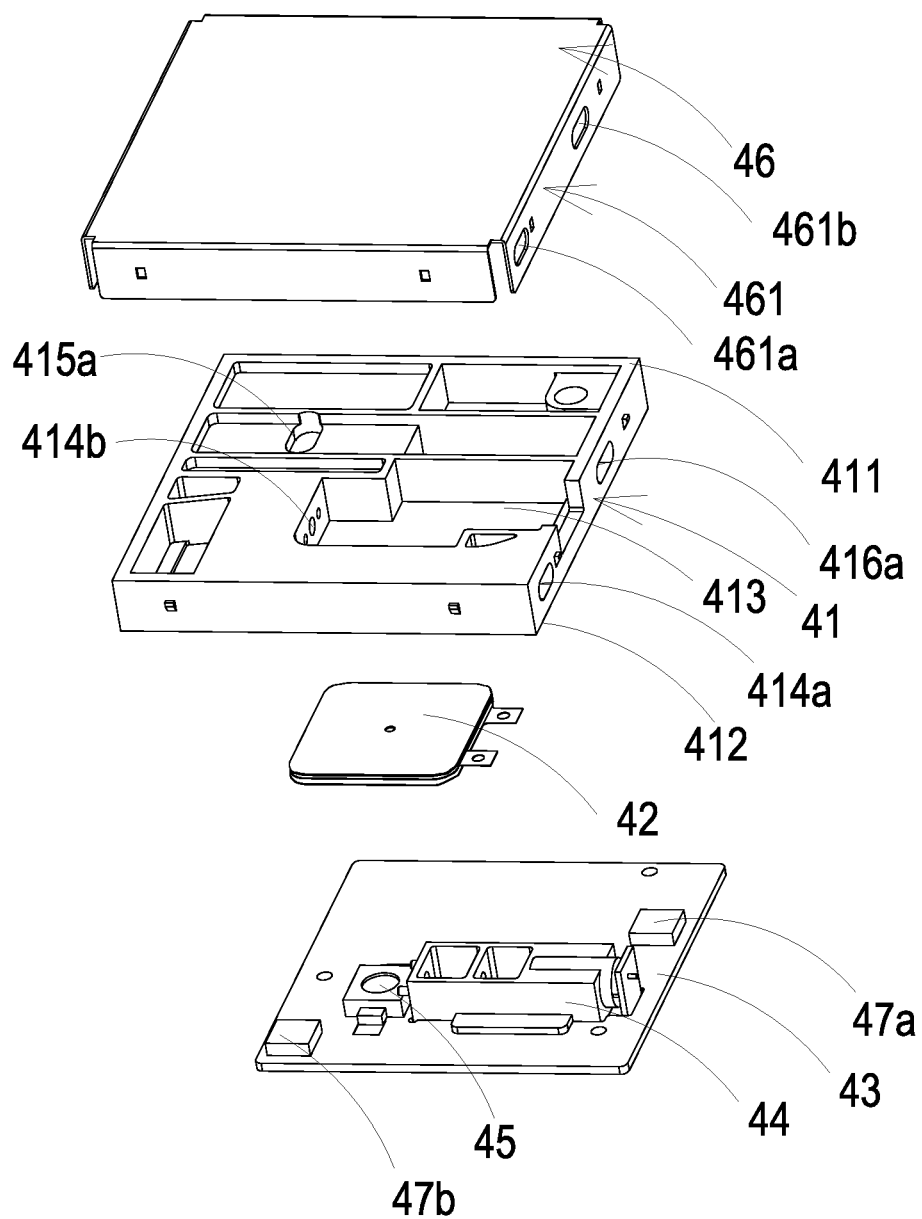
FIG. 5C is a schematic exploded view illustrating the gas detection main part of FIG. 5B.
Figure 7:
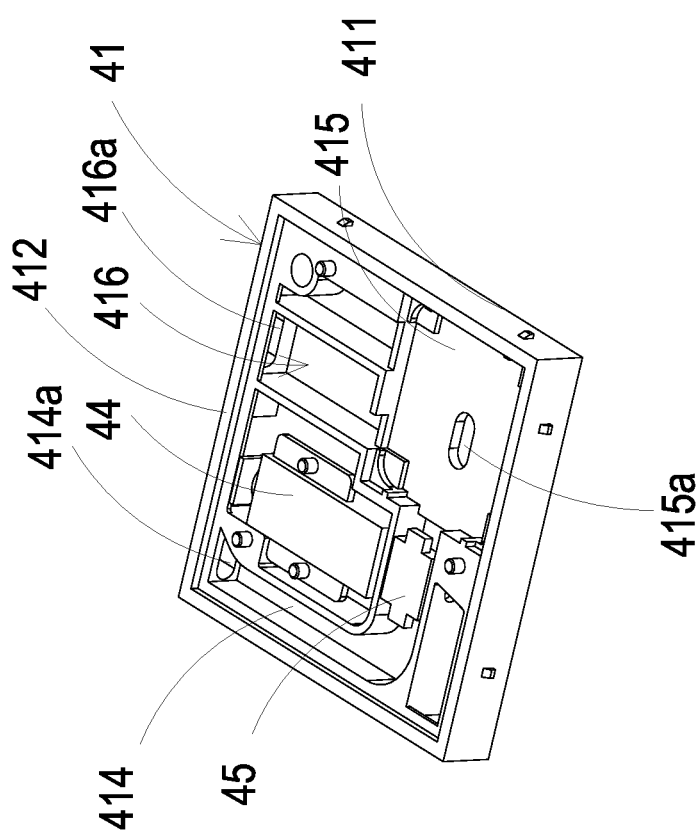
FIG. 7 is a schematic perspective view illustrating a laser component and a particulate sensor accommodated in the base of FIG. 5C.

Please refer to FIG. 5C and FIG. 7. In the embodiment, the laser component 44 and the particulate sensor 45 are disposed on the driving circuit board 43 and accommodated in the base 41. In order to clearly describe the positions of the laser component 44, the particulate sensor 45 and the base 41, the driving circuit board 43 is omitted in FIG. 7. Please refer to FIG. 5C, FIG. 6B, and FIG. 7, the laser component 44 is accommodated in the laser loading region 413 of the base 41, and the particulate sensor 45 is accommodated in the gas-inlet groove 414 of the base 41 and is aligned to the laser component 44. In addition, the laser component 44 is spatially corresponding to the transparent window 414b, a light beam emitted by the laser component 44 passes through the transparent window 414b and irradiates into the gas-inlet groove 414. A light beam path emitted from the laser component 44 passes through the transparent window 414b and extends in a direction perpendicular to the gas-inlet groove 414. In the embodiment, a projecting light beam emitted from the laser component 44 passes through the transparent window 414b and enters the gas-inlet groove 414, and suspended particles contained in the gas passing through the gas-inlet groove 414 is irradiated by the projecting light beam. When the suspended particles contained in the gas are irradiated and generate scattered light spots, the scattered light spots are received and calculated by the particulate sensor 45 for obtaining related information about the sizes and the concentration of the suspended particles contained in the gas. For example, the suspended particles contained in the gas include bacteria and viruses. In the embodiment, the particulate sensor 45 is a PM2.5 sensor.

Figure 8B:
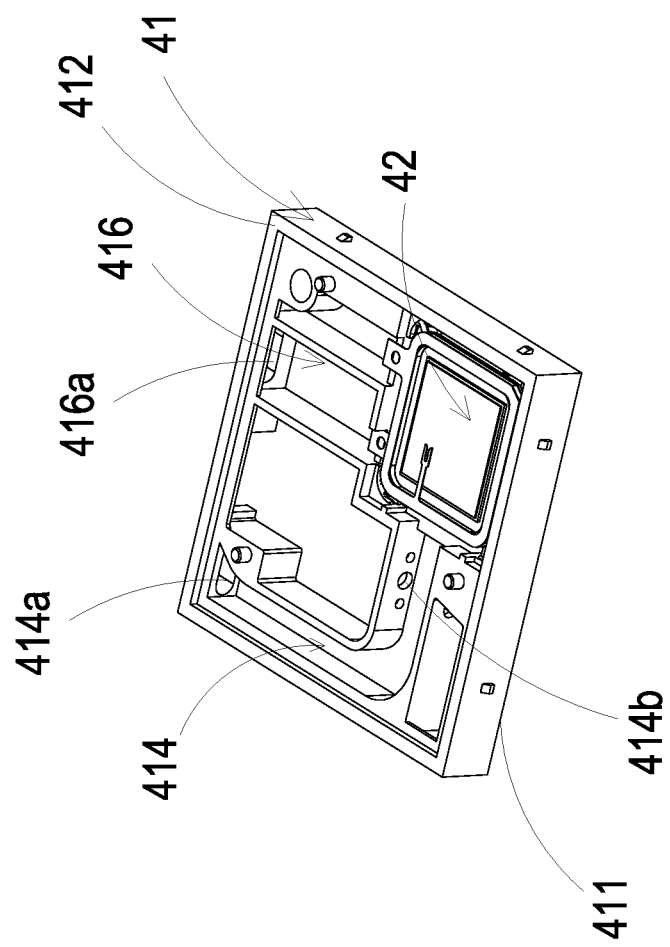
FIG. 8B is a schematic perspective view illustrating the combination of the piezoelectric actuator and the base of FIG. 5C.

Please refer to FIG. 8A and FIG. 8B. The piezoelectric-actuated element 42 is accommodated in the gas-guiding-component loading region 415 of the base 41. Preferably but not exclusively, the gas-guiding-component loading region 415 is square-shaped and includes four positioning protrusions 415b disposed at four corners of the gas-guiding-component loading region 415, respectively. The piezoelectric-actuated element 42 is disposed in the gas-guiding-component loading region 415 through the four positioning protrusions 415b. In addition, as shown in FIGS. 6A, 6B, 11B and 11C, the gas-guiding-component loading region 415 is in communication with the gas-inlet groove 414. When the piezoelectric-actuated element 42 is enabled, the gas in the gas-inlet groove 414 is inhaled by the piezoelectric-actuated element 42, so that the gas flows into the piezoelectric-actuated element 42, and the gas is transported into the gas-outlet groove 416 through the ventilation hole 415a of the gas-guiding-component loading region 415.

Please refer to FIGS. 5B and 5C. In the embodiment, the driving circuit board 43 covers and is attached to the second surface 412 of the base 41, and the laser component 44 is positioned and disposed on the driving circuit board 43, and is electrically connected to the driving circuit board 43. The particulate sensor 45 is positioned and disposed on the driving circuit board 43, and is electrically connected to the driving circuit board 43. As shown in FIG. 5B, when the outer cover 46 covers the base 41, the inlet opening 461a is spatially corresponding to the gas-inlet 414a of the base 41 (as shown in FIG. 11A), and the outlet opening 461b is spatially corresponding to the gas-outlet 416a of the base 41 (as shown in FIG. 11C).

Figure 9A:
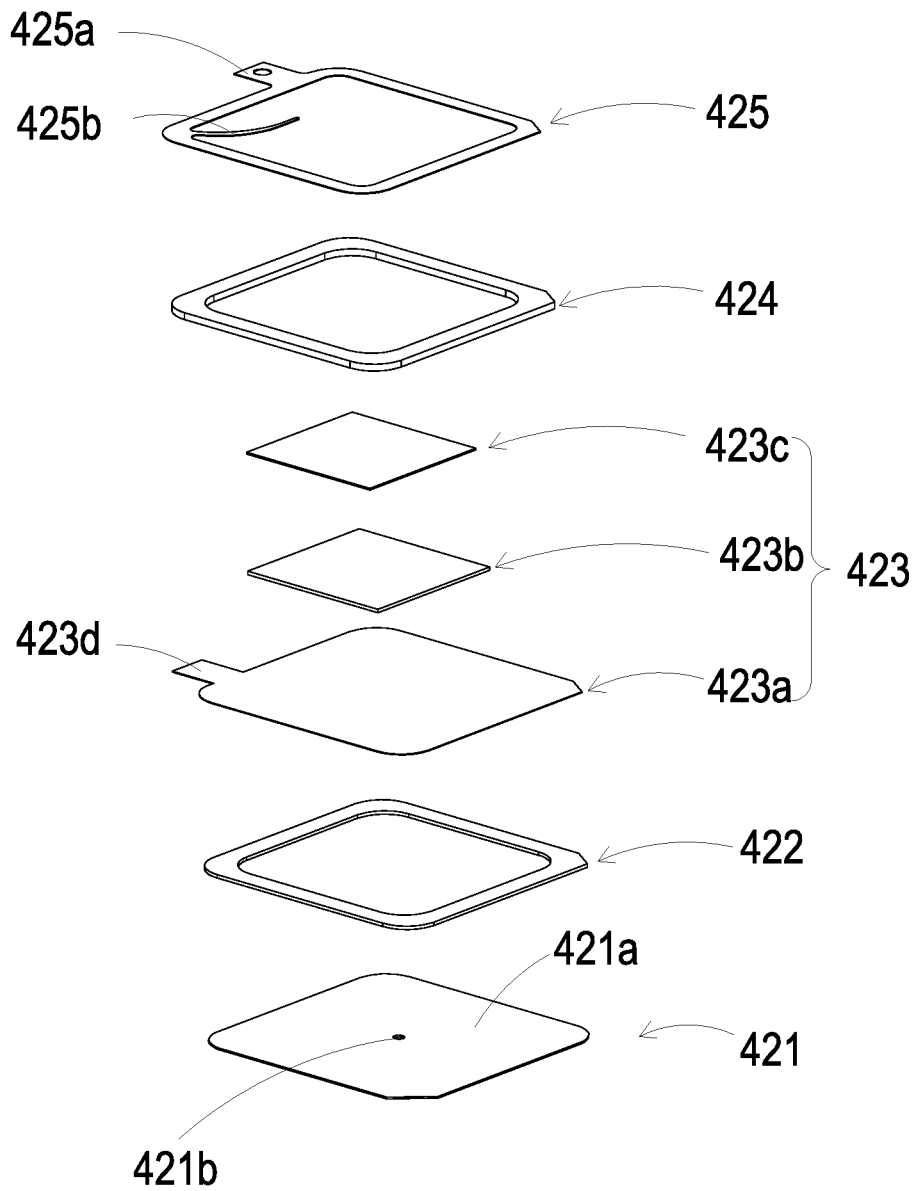
FIG. 9A is a schematic exploded front view illustrating the piezoelectric actuator of the gas detection main part of FIG. 5C.
Figure 9B:
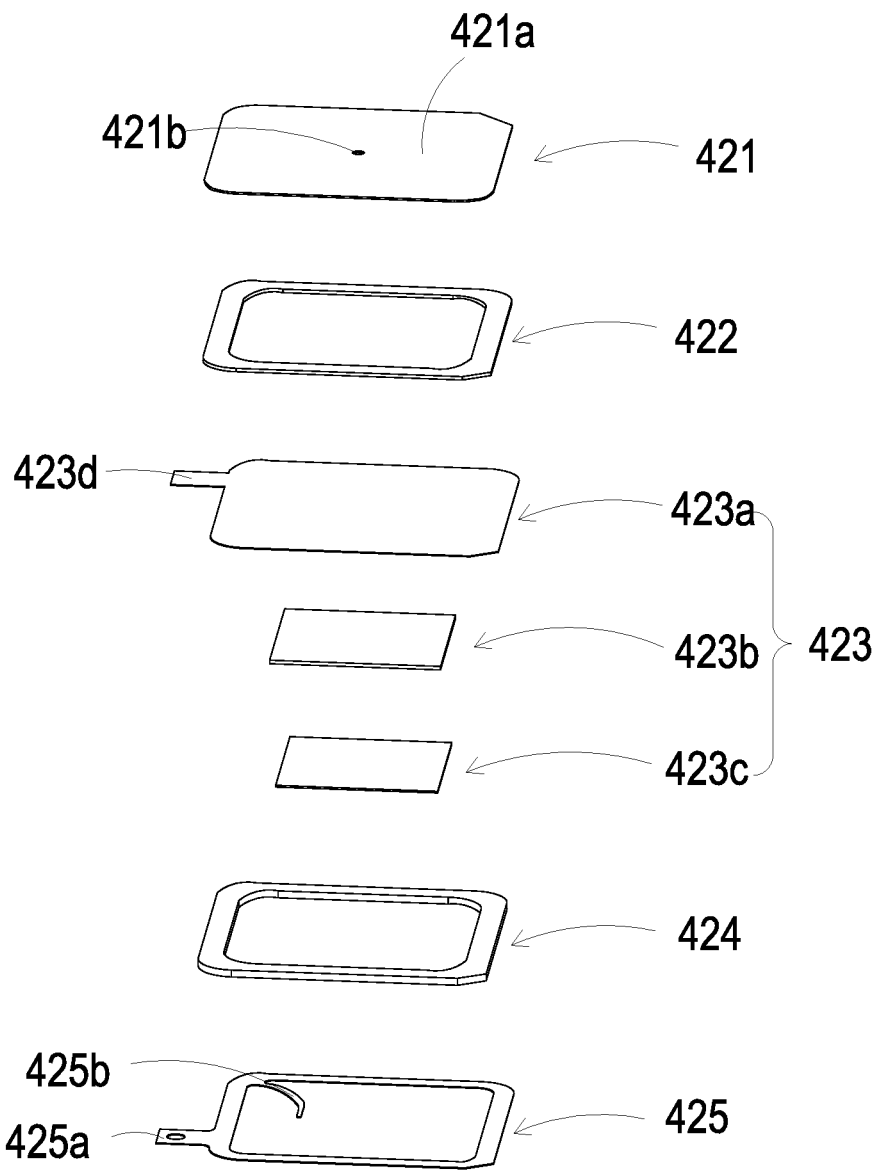
FIG. 9B is a schematic exploded rear view illustrating the piezoelectric actuator of the gas detection main part of FIG. 5C.

Please refer to FIGS. 9A and 9B. In the embodiment, the piezoelectric-actuated element 42 includes a gas-injection plate 421, a chamber frame 422, an actuator element 423, an insulation frame 424 and a conductive frame 425. In the embodiment, the gas-injection plate 421 is made by a flexible material and includes a suspension plate 421a and a hollow aperture 421b. The suspension plate 421a is a sheet structure and is permitted to undergo a bending deformation. Preferably but not exclusively, the shape and the size of the suspension plate 421a are corresponding to an inner edge of the gas-guiding-component loading region 415, but not limited thereto. The shape of the suspension plate 421a is selected from the group consisting of a square, a circle, an ellipse, a triangle and a polygon. The hollow aperture 421b passes through a center of the suspension plate 421a, so as to allow the gas to flow therethrough.

Figure 10A:
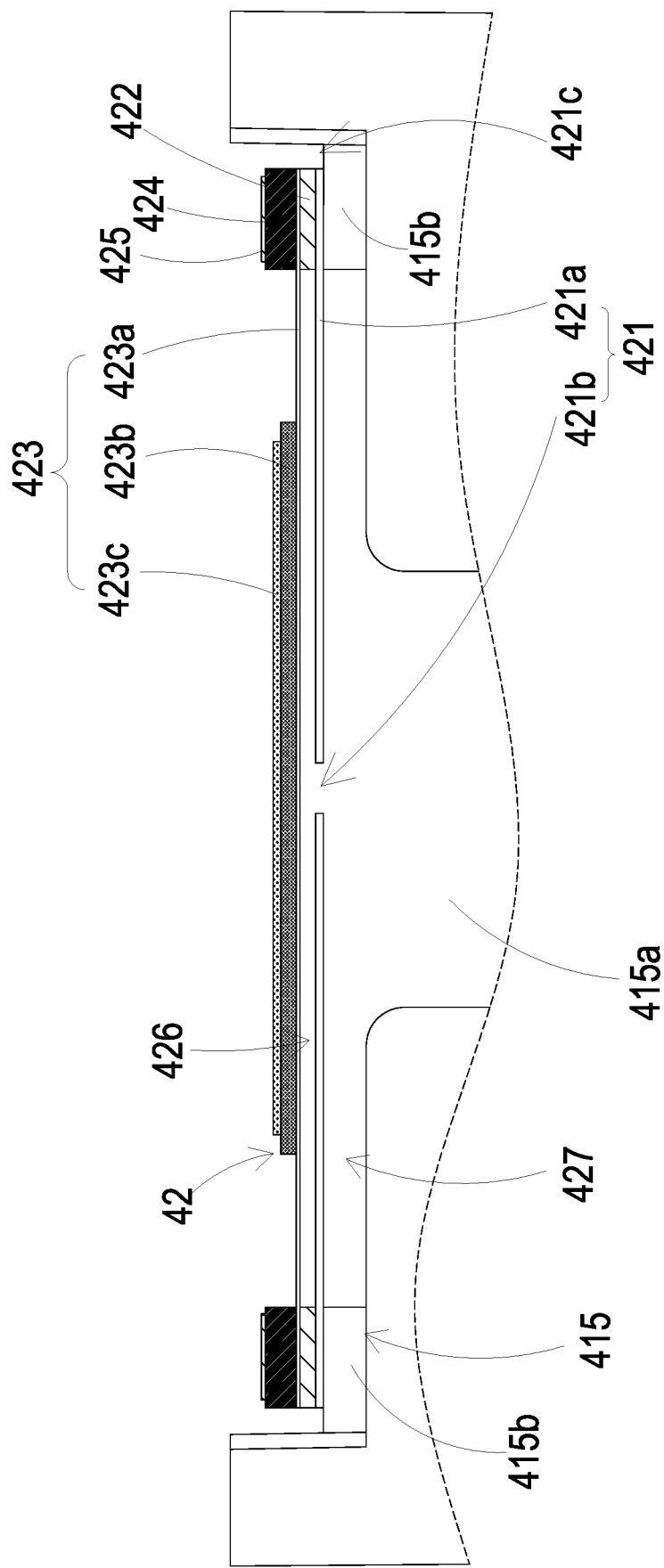
FIG. 10A is a schematic cross-sectional view illustrating the piezoelectric actuator of the gas detection main part accommodated in the gas-guiding-component loading region of FIG. 9A.

Please refer to FIG. 9A, FIG. 9B and FIG. 10A. In the embodiment, the chamber frame 422 is carried and stacked on the gas-injection plate 421. In addition, the shape of the chamber frame 422 is corresponding to the gas-injection plate 421. The actuator element 423 is carried and stacked on the chamber frame 422. A resonance chamber 426 is collaboratively defined by the actuator element 423, the chamber frame 422 and the suspension plate 421a, and is formed between the actuator element 423, the chamber frame 422 and the suspension plate 421a. The insulation frame 424 is carried and stacked on the actuator element 423 and the appearance of the insulation frame 424 is similar to that of the chamber frame 422. The conductive frame 425 is carried and stacked on the insulation frame 424, and the appearance of the conductive frame 425 is similar to that of the insulation frame 424. In addition, the conductive frame 425 includes a conducting pin 425a and a conducting electrode 425b. The conducting pin 425a is extended outwardly from an outer edge of the conductive frame 425, and the conducting electrode 425b is extended inwardly from an inner edge of the conductive frame 425. Moreover, the actuator element 423 further includes a piezoelectric carrying plate 423a, an adjusting resonance plate 423b and a piezoelectric plate 423c. The piezoelectric carrying plate 423a is carried and stacked on the chamber frame 422. The adjusting resonance plate 423b is carried and stacked on the piezoelectric carrying plate 423a. The piezoelectric plate 423c is carried and stacked on the adjusting resonance plate 423b. The adjusting resonance plate 423b and the piezoelectric plate 423c are accommodated in the insulation frame 424. The conducting electrode 425b of the conductive frame 425 is electrically connected to the piezoelectric plate 423c. In the embodiment, the piezoelectric carrying plate 423a and the adjusting resonance plate 423b are made by a conductive material. The piezoelectric carrying plate 423a includes a piezoelectric pin 423d. The piezoelectric pin 423d and the conducting pin 425a are electrically connected to a driving circuit (not shown) of the driving circuit board 43, so as to receive a driving signal, such as a driving frequency and a driving voltage. Through this structure, a circuit is formed by the piezoelectric pin 423d, the piezoelectric carrying plate 423a, the adjusting resonance plate 423b, the piezoelectric plate 423c, the conducting electrode 425b, the conductive frame 425 and the conducting pin 425a for transmitting the driving signal. Moreover, the insulation frame 424 is insulated between the conductive frame 425 and the actuator element 423, so as to avoid the occurrence of a short circuit. Thereby, the driving signal can be transmitted to the piezoelectric plate 423c. After receiving the driving signal such as the driving frequency and the driving voltage, the piezoelectric plate 423c deforms due to the piezoelectric effect, and the piezoelectric carrying plate 423a and the adjusting resonance plate 423b are further driven to generate the bending deformation in the reciprocating manner.

As described above, the adjusting resonance plate 423b is located between the piezoelectric plate 423c and the piezoelectric carrying plate 423a and served as a cushion between the piezoelectric plate 423c and the piezoelectric carrying plate 423a. Thereby, the vibration frequency of the piezoelectric carrying plate 423a is adjustable. Basically, the thickness of the adjusting resonance plate 423b is greater than the thickness of the piezoelectric carrying plate 423a, and the thickness of the adjusting resonance plate 423b is adjustable, thereby the vibration frequency of the actuator element 423 can be adjusted accordingly.

Please refer to FIG. 9A, FIG. 9B and FIG. 10A. In the embodiment, the gas-injection plate 421, the chamber frame 422, the actuator element 423, the insulation frame 424 and the conductive frame 425 are stacked and positioned in the gas-guiding-component loading region 415 sequentially, so that the piezoelectric-actuated element 42 is supported and positioned in the gas-guiding-component loading region 415. The bottom of the gas-injection plate 421 is fixed on the four positioning protrusions 415b of the gas-guiding-component loading region 415 for supporting and positioning, so that a plurality of vacant spaces 421c are defined between the suspension plate 421a of the gas-injection plate 421 and an inner edge of the gas-guiding-component loading region 415 for gas flowing therethrough.

Please refer to FIG. 10A. A flowing chamber 427 is formed between the gas-injection plate 421 and the bottom surface of the gas-guiding-component loading region 415. The flowing chamber 427 is in communication with the resonance chamber 426 between the actuator element 423, the chamber frame 422 and the suspension plate 421a through the hollow aperture 421b of the gas-injection plate 421. By controlling the vibration frequency of the gas in the resonance chamber 426 to be close to the vibration frequency of the suspension plate 421a, the Helmholtz resonance effect is generated between the resonance chamber 426 and the suspension plate 421a, so as to improve the efficiency of gas transportation.

Figure 10B:
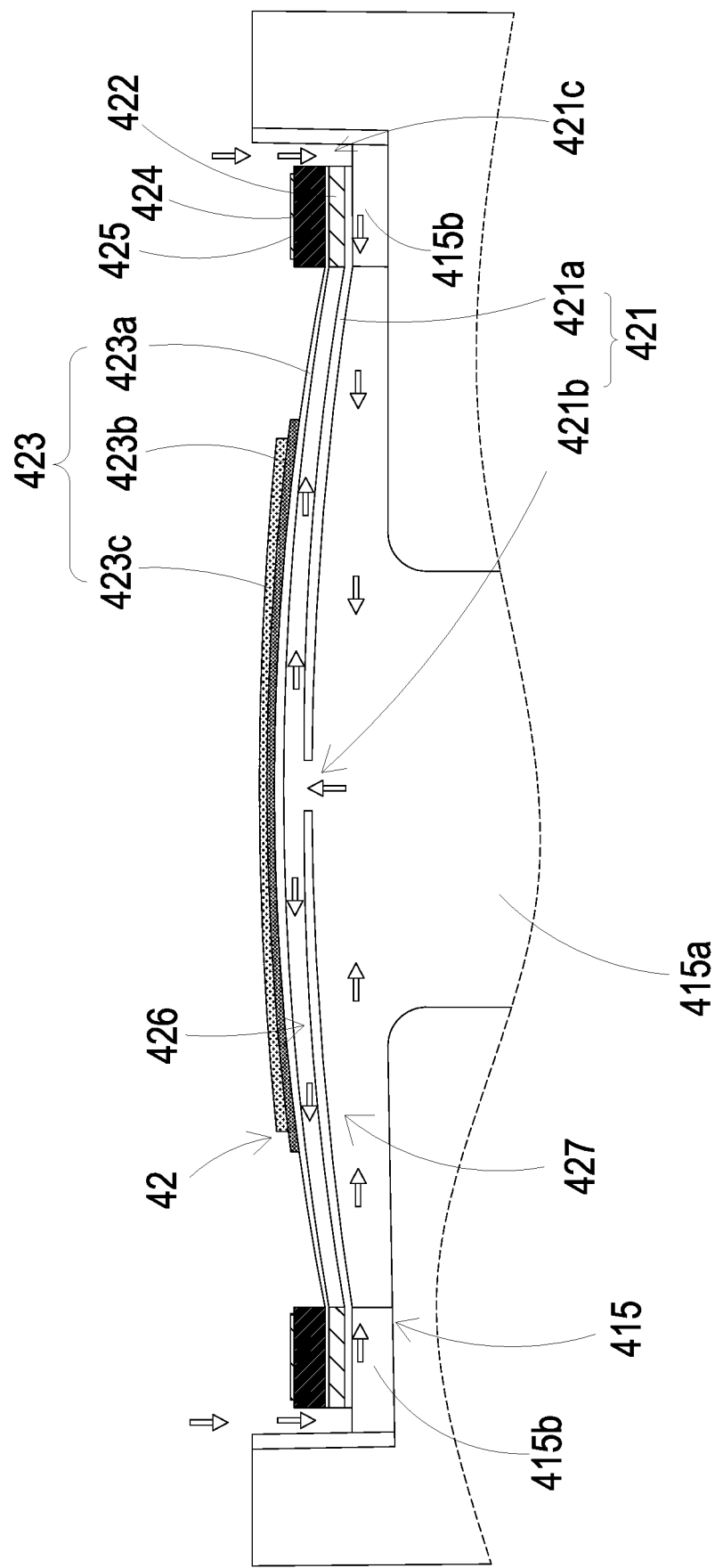
FIGS. 10B and 10C schematically illustrate the operation steps of the piezoelectric actuator of FIG. 10A.
Figure 10C:
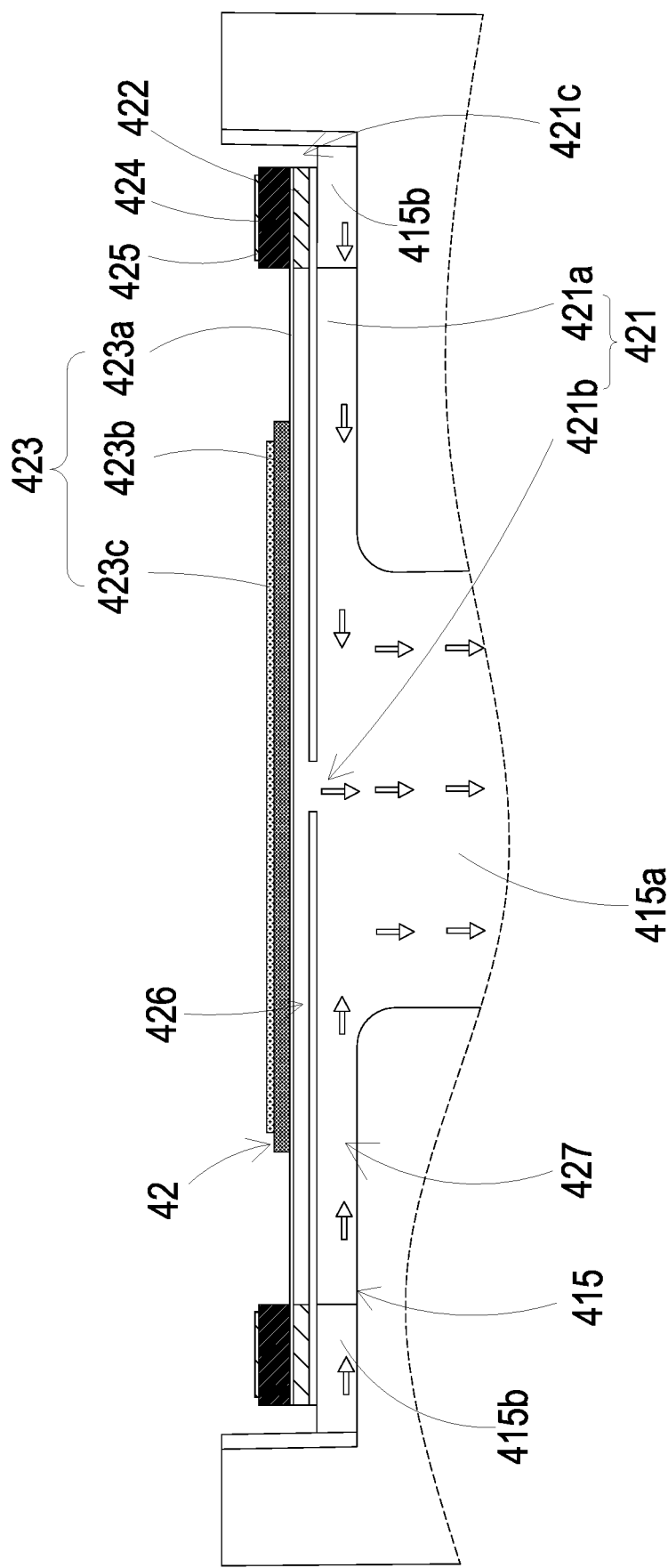

Please refer to FIG. 10B. When the piezoelectric plate 423c is moved away from the bottom surface of the gas-guiding-component loading region 415, the suspension plate 421a of the gas-injection plate 421 is driven to move away from the bottom surface of the gas-guiding-component loading region 415 by the piezoelectric plate 423c. In that, the volume of the flowing chamber 427 is expanded rapidly, the internal pressure of the flowing chamber 427 is decreased to form a negative pressure, and the gas outside the piezoelectric-actuated element 42 is inhaled through the vacant spaces 421c and enters the resonance chamber 426 through the hollow aperture 421b. Consequently, the pressure in the resonance chamber 426 is increased to generate a pressure gradient. Further as shown in FIG. 10C, when the suspension plate 421a of the gas-injection plate 421 is driven by the piezoelectric plate 423c to move toward the bottom surface of the gas-guiding-component loading region 415, the gas in the resonance chamber 426 is discharged out rapidly through the hollow aperture 421b, and the gas in the flowing chamber 427 is compressed, thereby the converged gas is quickly and massively ejected out of the flowing chamber 427 under the condition close to an ideal gas state of the Benulli's law, and transported to the ventilation hole 415a of the gas-guiding-component loading region 415. By repeating the above operation steps shown in FIG. 10B and FIG. 10C, the piezoelectric plate 423c is driven to generate the bending deformation in a reciprocating manner. According to the principle of inertia, since the gas pressure inside the resonance chamber 426 is lower than the equilibrium gas pressure after the converged gas is ejected out, the gas is introduced into the resonance chamber 426 again. Moreover, the vibration frequency of the gas in the resonance chamber 426 is controlled to be close to the vibration frequency of the piezoelectric plate 423c, so as to generate the Helmholtz resonance effect to achieve the gas transportation at high speed and in large quantities.

Furthermore, as shown in FIG. 11A, the gas is inhaled through the inlet opening 461a of the outer cover 46, flows into the gas-inlet groove 414 of the base 41 through the gas-inlet 414a, and is transported to the position of the particulate sensor 45. Further as shown in FIG. 11B, the piezoelectric-actuated element 42 is enabled continuously to inhale the gas into the gas-inlet path, and facilitate the gas to be introduced rapidly and stably, and transported above the particulate sensor 45. At this time, a projecting light beam emitted from the laser component 44 passes through the transparent window 414b to irradiate the suspended particles contained in the gas flowing above the particulate sensor 45 in the gas-inlet groove 414. When the suspended particles contained in the gas are irradiated and generate scattered light spots, the scattered light spots are received and calculated by the particulate sensor 45 for obtaining related information about the sizes and the concentration of the suspended particles contained in the gas. Moreover, the gas above the particulate sensor 45 is continuously driven and transported by the piezoelectric-actuated element 42, flows into the ventilation hole 415a of the gas-guiding-component loading region 415, and is transported to the first section 416b of the gas-outlet groove 416. As shown in FIG. 11C, after the gas flows into the first section 416b of the gas-outlet groove 416, the gas is continuously transported into the first section 416b by the piezoelectric-actuated element 42, and the gas in the first section 416b is pushed to the second section 416c. Finally, the gas is discharged out through the gas-outlet 416a and the outlet opening 461b.

Figure 12:
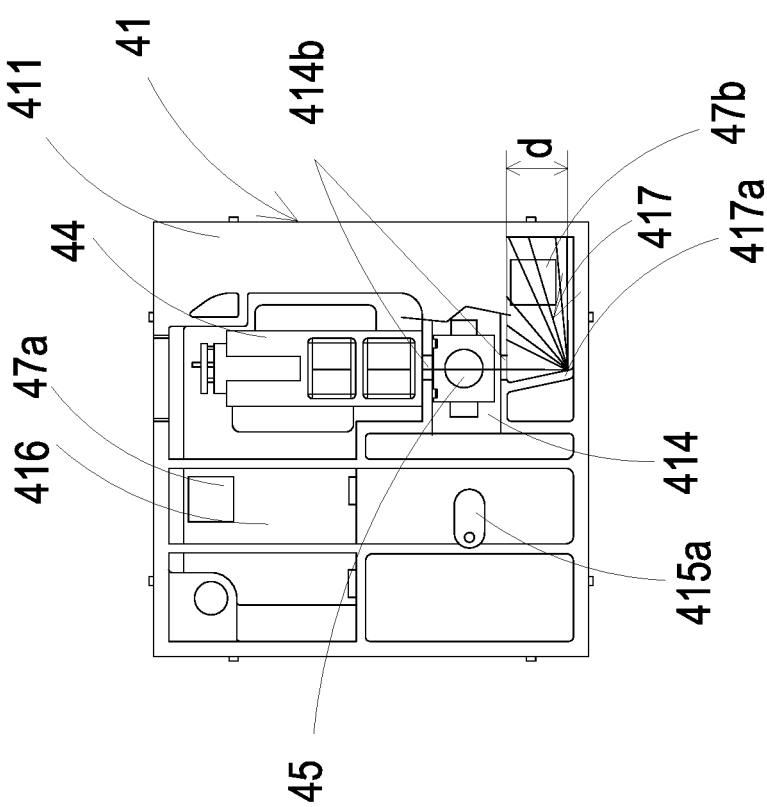
FIG. 12 schematically illustrates a light beam path emitted from the laser component of the gas detection main part of FIG. 5C.

As shown in FIG. 12, the base 41 further includes a light trapping region 417. The light trapping region 417 is hollowed out from the first surface 411 to the second surface 412 and is spatially corresponding to the laser loading region 413. In the embodiment, the light beam emitted by the laser component 44 is projected into the light trapping region 417 through the transparent window 414b. The light trapping region 417 includes a light trapping structure 417a having an oblique cone surface. The light trapping structure 417a is spatially corresponding to the light beam path emitted from the laser component 44. In addition, the projecting light beam emitted from the laser component 44 is reflected into the light trapping region 417 through the oblique cone surface of the light trapping structure 417a, so as to prevent the projecting light beam from reflecting back to the position of the particulate sensor 45. In the embodiment, a light trapping distance d is maintained between the transparent window 414b and a position where the light trapping structure 417a receives the projecting light beam, so as to avoid the projecting light beam projected on the light trapping structure 417a from reflecting back to the position of the particulate sensor 45 directly due to excessive stray light generated after reflection and result in distortion of detection accuracy.

Please refer to FIG. 5C and FIG. 12. The gas detection module 4 of the present disclosure not only detects the suspended particles in the gas, but also detects the characteristics of the introduced gas. Preferably but not exclusively, the gas can be detected is selected from the group consisting of formaldehyde, ammonia, carbon monoxide, carbon dioxide, oxygen, ozone and a combination thereof. In the embodiment, the gas detection module 4 further includes a first volatile-organic-compound sensor 47a. The first volatile-organic-compound sensor 47a positioned and disposed on the driving circuit board 43 is electrically connected to the driving circuit board 43, and accommodated in the gas-outlet groove 416, so as to detect the gas flowing through the gas-outlet path of the gas-outlet groove 416. Thus, the concentration or the characteristics of volatile organic compounds contained in the gas in the gas-outlet path can be detected. Alternatively, in an embodiment, the gas detection module 4 further includes a second volatile-organic-compound sensor 47b. The second volatile-organic-compound sensor 47b positioned and disposed on the driving circuit board 43 is electrically connected to the driving circuit board 43 and is accommodated in the light trapping region 417. Thus, the concentration or the characteristics of volatile organic compounds contained in the gas flowing through the gas-inlet path of the gas-inlet groove 414 and transported into the light trapping region 417 through the transparent window 414b is detected.

In summary, the present disclosure provides a purification device for exercise environment. A gas detection module is utilized to monitor the air quality in the exercise environment with the exerciser at any time, and a purification unit is utilized to provide a solution for purifying and improving the air quality. In this way, the gas detection module and the purification unit combined with a gas guider can export a gas at a specific airflow amount, so as to achieve the filtering operation of purification unit and generate a purified gas. In addition, the gas guider constantly controls the airflow rate within 3 minutes to reduce the particle concentration of the suspended particles contained in the purified gas to less than 0.75 $\mu g/m^3$, so as to achieve the purification effect of safe filtration. Moreover, the gas detection module is used to detect the purified gas in the breathing region around the nose of the exerciser in the exercise environment, so as to provide the purified gas through safe filtration to the exerciser for breathing under an exercise state and obtain real-time information. When the particle concentration is too high, a warning notification can be sent to the exerciser in the exercise environment to alarm and notice him to immediately take preventive measures, such as stop exercising or providing an isolation cover to keep exercising there.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A purification device for exercise environment applied in an exercise environment, comprising:
    a main body comprising at least one gas inlet and at least one gas outlet, wherein the main body is a directional gas-guiding device fixedly combined with an exercise equipment in the exercise environment, wherein a directional guiding element is disposed in the at least one gas outlet of the main body, so that the purified gas is directionally filtered by the purification unit and discharged from the at least one outlet;

a purification unit disposed in the main body for purifying a gas introduced into the main body through the at least one gas inlet;

a gas guider disposed in the main body and adjacent to the at least one gas outlet, wherein the gas outside the main body is inhaled and flows through the purification unit for filtering and purifying, so that a purified gas is filtered and discharged out through the at least one outlet; and a gas detection module disposed in the main body for detecting a particle concentration of suspended particle contained in the purified gas filtered by the purification unit, wherein the gas guider is constantly controlled to operate and export the gas at an airflow rate within 3 minutes to reduce the particle concentration of the suspended particles contained in the purified gas to less than 0.75 $\mu g/m^3$, so as to provide the purified gas through safe filtration to an exerciser for breathing in the exercise environment.

2. The purification device for exercise environment according to claim 1, wherein the main body comprises a gas-flow channel disposed between the at least one gas inlet and the at least one gas outlet, wherein the purification unit is disposed in the gas-flow channel, and the gas guider is disposed in the gas-flow channel and located at a side of the purification unit, so that the gas outside the main body is inhaled through the at least one gas inlet, flows through the purification unit for filtering to generate the purified gas, and is discharged out through the at least one gas outlet.

3. The purification device for exercise environment according to claim 1, wherein the purification unit is a high efficiency particulate air filter screen.

4. The purification device for exercise environment according to claim 3, wherein the high efficiency particulate air filter screen is coated with a layer of a cleansing factor containing chlorine dioxide to inhibit viruses and bacteria in the gas introduced from an outside of the main body.

5. The purification device for exercise environment according to claim 3, wherein the high efficiency particulate air filter screen is coated with an herbal protective layer consisting of Rhus chinensis Mill extracts from Japan and Ginkgo biloba extracts to form an herbal protective anti-allergic filter which can effectively resist allergy and destroy a surface protein of influenza virus in the gas introduced from an outside of the main body through the high efficiency particulate air filter screen.

6. The purification device for exercise environment according to claim 3, wherein the high efficiency particulate air filter screen is coated with a silver ion to inhibit viruses and bacteria contained in the gas introduced from an outside of the main body.

7. The purification device for exercise environment according to claim 1, wherein the gas guider is a fan.

8. The purification device for exercise environment according to claim 1, wherein the gas guider is an actuating pump, the actuating pump comprises:

a gas inlet plate having at least one gas inlet aperture, at least one convergence channel, and a convergence chamber, wherein the at least one gas inlet aperture is disposed to inhale the gas outside the main body, the at least one gas inlet aperture correspondingly penetrates through the gas inlet plate into the at least one convergence channel, and the at least one convergence channel is converged into the convergence chamber, so that the gas inhaled through the at least one gas inlet aperture is converged into the convergence chamber;

a resonance plate disposed on the at least one gas inlet plate and having a central aperture, a movable part and a fixed part, wherein the central aperture is disposed at a center of the resonance plate, and is corresponding in position to the convergence chamber of the gas inlet plate, the movable part surrounds the central aperture and is corresponding in position to the convergence chamber, and the fixed part surrounds the movable part and is fixedly attached on the gas inlet plate; and a piezoelectric actuator connected to the resonance plate and corresponding in position to the resonance plate, wherein the piezoelectric actuator comprises a suspension plate, an outer frame, at least one bracket and a piezoelectric element, wherein the suspension plate is permitted to undergo a bending deformation, the outer frame surrounds the suspension plate, the at least one bracket is connected between the suspension plate and the outer frame to provide an elastic support for the suspension plate, and the piezoelectric element is attached to a surface of the suspension plate, wherein when a voltage is applied to the piezoelectric element, the suspension plate is driven to undergo the bending deformation, wherein a chamber space is formed between the resonance plate and the piezoelectric actuator, so that when the piezoelectric actuator is driven, the gas outside the main body introduced from the gas inlet aperture of the gas inlet plate is converged to the convergence chamber through the at least one convergence channel, and flows through the central aperture of the resonance plate so as to generate a resonance effect by the movable part of the resonance plate and the piezoelectric actuator to transport the gas.

9. The purification device for exercise environment according to claim 1, wherein the gas detection module comprises a controlling circuit board, a gas detection main part, a microprocessor and a communicator, and the gas detection main part, the microprocessor and the communicator are integrally packaged on the controlling circuit board and electrically connected to the controlling circuit board, wherein the microprocessor receives a detection datum of the particle concentration of the suspended particles contained in the purified gas from the gas detection module for calculating and processing, and controls to enable and disable the operations of the gas guider for gas filtering and purifying, wherein the communicator transmits the detection datum of the particle concentration received from the microprocessor to an external device, so that the external device obtains and records the detection datum of the particle concentration of the purified gas, issues an alarm and/or notification, and feeds back to the purification device for exercise environment to adjust the airflow rate of the gas guider.

10. The purification device for exercise environment according to claim 9, wherein the gas detection main part comprises:

a base comprising:

a first surface;

a second surface opposite to the first surface;

a laser loading region hollowed out from the first surface to the second surface;

a gas-inlet groove concavely formed from the second surface and disposed adjacent to the laser loading region, wherein the gas-inlet groove comprises a gas-inlet and two lateral walls, the gas-inlet is in communication with an environment outside the base, and a transparent window is opened on the two lateral walls and is in communication with the laser loading region;

a gas-guiding-component loading region concavely formed from the second surface and in communication with the gas-inlet groove, wherein a ventilation hole penetrates a bottom surface of the gas-guiding-component loading region, and the gas-guiding-component loading region has four positioning protrusions disposed at four corners thereof; and a gas-outlet groove concavely formed from the first surface, spatially corresponding to the bottom surface of the gas-guiding-component loading region, and hollowed out from the first surface to the second surface in a region where the first surface is not aligned with the gas-guiding-component loading region, wherein the gas-outlet groove is in communication with the ventilation hole, and a gas-outlet is disposed in the gas-outlet groove and in communication with the environment outside the base;

a piezoelectric-actuated element accommodated in the gas-guiding-component loading region;

a driving circuit board covering and attached to the second surface of the base;

a laser component positioned and disposed on the driving circuit board, electrically connected to the driving circuit board, and accommodated in the laser loading region, wherein a light beam path emitted from the laser component passes through the transparent window and extends in a direction perpendicular to the gas-inlet groove;

a particulate sensor positioned and disposed on the driving circuit board, electrically connected to the driving circuit board, and disposed at an position where the gas-inlet groove orthogonally intersects with the light beam path of the laser component, so that the suspended particles in the purified gas passing through the gas-inlet groove and irradiated by a projecting light beam emitted from the laser component are detected; and an outer cover covering the first surface of the base and including a side plate, wherein the side plate has an inlet opening spatially corresponding to the gas-inlet and an outlet opening spatially corresponding to the gas-outlet, wherein the first surface of the base is covered with the outer cover, and the second surface of the base is covered with the driving circuit board, so that a gas-inlet path is defined by the gas-inlet groove, and an gas-outlet path is defined by the gas-outlet groove, so that the gas is inhaled from the environment outside the base by the piezoelectric-actuated element, transported into the gas-inlet path defined by the gas-inlet groove through the inlet opening, and passes through the particulate sensor to detect the concentration of the suspended particles contained in the gas, and the gas transported through the piezoelectric-actuated element is transported out of the gas-outlet path defined by the gas-outlet groove through the ventilation hole and then discharged through the outlet opening.

11. The purification device for exercise environment according to claim 10, wherein the piezoelectric-actuated element comprises:

a gas-injection plate comprising a suspension plate and a hollow aperture, wherein the suspension plate is permitted to undergo a bending deformation, and the hollow aperture is formed at a center of the suspension plate;

a chamber frame carried and stacked on the suspension plate;

an actuator element carried and stacked on the chamber frame, wherein the actuator element comprises:
a piezoelectric carrying plate carried and stacked on the chamber frame;

an adjusting resonance plate carried and stacked on the piezoelectric carrying plate; and a piezoelectric plate carried and stacked on the adjusting resonance plate, wherein the piezoelectric plate is configured to drive the piezoelectric carrying plate and the adjusting resonance plate to generate the bending deformation in a reciprocating manner when a voltage is applied thereto, an insulation frame carried and stacked on the actuator element; and a conductive frame carried and stacked on the insulation frame, wherein the gas-injection plate is fixed on the four positioning protrusions of the gas-guiding-component loading region for supporting and positioning, so that a vacant space is defined and outside of the gas-injection plate and surrounding the gas-injection plate for the gas flowing therethrough, a flowing chamber is formed between the gas-injection plate and the bottom surface of the gas-guiding-component loading region, and a resonance chamber is formed between the actuator element, the chamber frame and the suspension plate, wherein when the actuator element is enabled to drive the gas-injection plate to move and generates a resonance effect, the suspension plate of the gas-injection plate is driven to generate the bending deformation in a reciprocating manner, the gas is inhaled through the vacant space, flows into the flowing chamber, and then discharges out, so as to complete gas transportation.

12. The purification device for exercise environment according to claim 11, further comprising a first volatile-organic-compound sensor positioned disposed on the driving circuit board, electrically connected to the driving circuit board, and accommodated in the gas-outlet groove, so as to detect volatile organic gases contained in the purified gas flowing through the gas-outlet path of the gas-outlet groove.

13. The purification device for exercise environment according to claim 1, wherein the airflow rate discharged by the gas guider is at least 800 ft$^3$/min, and a breathing distance between the at least one gas outlet of the main body and a breathing region around a nose region of the exerciser is maintained, and the breathing distance is ranged from 60 cm to 200 cm.

14. The purification device for exercise environment according to claim 1, further comprises an isolation cover covering the exercise equipment and the exerciser, the isolation cover comprises an opening, wherein the main body runs through and fixes in the opening, the at least one gas inlet of the main body is located outside of the isolation cover, and the at least one gas outlet is located inside the isolation cover.

15. The purification device for exercise environment according to claim 14, wherein the airflow rate discharged by the gas guider is lower than 800 ft$^3$/min.

* * * * *